United States Patent
Nagae et al.

(10) Patent No.: US 10,762,634 B2
(45) Date of Patent: Sep. 1, 2020

(54) IMAGE PROCESSING DEVICE AND X-RAY DIAGNOSTIC APPARATUS

(71) Applicant: Toshiba Medical Systems Corporation, Otawara-Shi (JP)

(72) Inventors: Ryoichi Nagae, Nasushiobara (JP); Yasuto Hayatsu, Otawara (JP); Yoshiaki Iijima, Nasushiobara (JP); Naoki Uchida, Utsunomiya (JP); Yoshinori Shimizu, Nasushiobara (JP); Yuichiro Watanabe, Yaita (JP); Takuya Sakaguchi, Utsunomiya (JP)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/837,203

(22) Filed: Aug. 27, 2015

(65) Prior Publication Data

US 2016/0078621 A1     Mar. 17, 2016

(30) Foreign Application Priority Data

Sep. 11, 2014   (JP) .................................. 2014-184892

(51) Int. Cl.
    *G06T 7/00*    (2017.01)
    *A61B 6/00*    (2006.01)

(52) U.S. Cl.
    CPC .......... *G06T 7/0016* (2013.01); *A61B 6/4441* (2013.01); *A61B 6/463* (2013.01);
    (Continued)

(58) Field of Classification Search
    CPC ....... A61B 6/4441; A61B 6/463; A61B 6/481; A61B 6/485; A61B 6/501; A61B 6/504;
    (Continued)

(56) References Cited

U.S. PATENT DOCUMENTS

| 6,052,476 A * | 4/2000 | Qian ...................... A61B 6/463 378/209 |
| 8,929,632 B2 * | 1/2015 | Horz ...................... A61B 6/481 382/130 |

(Continued)

FOREIGN PATENT DOCUMENTS

| JP | 5140309 | 2/2013 |
| JP | 2014-12133 | 1/2014 |

OTHER PUBLICATIONS

Gölitz et al. "Parametric color coding of digital subtraction angiography in the evaluation of carotid cavernous fistulas." Clinical neuroradiology 23.2 (2013): 113-120. (Year: 2013).*

(Continued)

*Primary Examiner* — Katrina R Fujita
(74) *Attorney, Agent, or Firm* — Oblon, McClelland, Maier & Neustadt, L.L.P.

(57) ABSTRACT

According to one embodiment, an image processing device includes processing circuitry. The processing circuitry sequentially acquires image data of time-sequential DSA images of an object, and acquires a parameter value for each pixel based on temporal change of a pixel value of the each pixel corresponding to the same region of the object in the sequentially acquired image data of time-sequential DSA images. Further, the processing circuitry sequentially generates image data of parameter images in such a manner that identification information according to the parameter value is assigned to the each pixel corresponding to the same region of the object, each time image data of a DSA image of the latest time phase being acquired.

15 Claims, 14 Drawing Sheets

(52) U.S. Cl.
CPC .............. *A61B 6/481* (2013.01); *A61B 6/485* (2013.01); *A61B 6/487* (2013.01); *A61B 6/501* (2013.01); *A61B 6/504* (2013.01); *A61B 6/507* (2013.01); *A61B 6/5217* (2013.01); *A61B 6/5235* (2013.01); *G06T 2207/10116* (2013.01); *G06T 2207/10121* (2013.01); *G06T 2207/20224* (2013.01); *G06T 2207/30104* (2013.01)

(58) Field of Classification Search
CPC ..... A61B 6/507; A61B 6/5217; A61B 6/5235; G06T 7/0016; G06T 2207/10116; G06T 2207/10121; G06T 2207/20224; G06T 2207/30104
See application file for complete search history.

(56) References Cited

U.S. PATENT DOCUMENTS

| | | | |
|---|---|---|---|
| 8,948,475 B2 | 2/2015 | Ostermeier et al. | |
| 2008/0027316 A1* | 1/2008 | Baumgart | A61B 6/463 600/425 |
| 2008/0095422 A1* | 4/2008 | Suri | G06K 9/6206 382/131 |
| 2009/0010512 A1* | 1/2009 | Zhu | A61B 6/481 382/130 |
| 2009/0110252 A1* | 4/2009 | Baumgart | A61B 6/481 382/130 |
| 2009/0192385 A1* | 7/2009 | Meissner | A61B 6/032 600/426 |
| 2009/0279766 A1 | 11/2009 | Heigl et al. | |
| 2010/0053209 A1 | 3/2010 | Rauch et al. | |
| 2010/0166281 A1* | 7/2010 | Burger | A61B 6/032 382/131 |
| 2010/0329523 A1* | 12/2010 | Ostermeier | A61B 6/463 382/128 |
| 2011/0213244 A1* | 9/2011 | Frinking | A61B 5/055 600/431 |
| 2012/0148139 A1* | 6/2012 | Ozawa | A61B 6/504 382/132 |
| 2013/0077839 A1* | 3/2013 | Horz | G06T 11/001 382/130 |
| 2013/0190615 A1* | 7/2013 | Royalty | A61B 6/481 600/431 |
| 2014/0200461 A1* | 7/2014 | Zhang | A61B 6/481 600/481 |
| 2015/0071520 A1 | 3/2015 | Takemoto et al. | |
| 2016/0022236 A1* | 1/2016 | Ohishi | A61B 6/481 600/431 |

OTHER PUBLICATIONS

Strother et al. "Parametric color coding of digital subtraction angiography." American Journal of Neuroradiology 31.5 (2010): 919-924. (Year: 2010).*

Combined Office Action and Search Report dated Aug. 27, 2018 in Chinese Patent Application No. 201510569957.2, 10 pages (with English translation of categories of cited documents).

Office Action dated May 8, 2018 in Japanese Patent Application No. 2014-184892.

Chinese Office Action dated Dec. 25, 2017 in Chinese Application No. 201510569957.2, 7 pages.

* cited by examiner

IMAGE PROCESSING DEVICE AND X-RAY DIAGNOSTIC APPARATUS

CROSS-REFERENCE TO RELATED APPLICATIONS

This application claims the benefit of priority of Japanese Patent Application No. 2014-184892, filed Sep. 11, 2014, the entire contents of which are incorporated herein by reference.

FIELD

Embodiments described herein relate generally to an image processing device and an X-ray diagnostic apparatus.

BACKGROUND

As a technique of obtaining blood flow information inside a patient body, fluoroscopic imaging with the use of contrast agent and an X-ray diagnostic apparatus is known. As an example in fluoroscopic imaging, DSA (Digital Subtraction Angiography) images are acquired by time-sequentially imaging the same region of a patient using an X-ray diagnostic apparatus before and after administration of contrast agent. Specifically, subtraction images corresponding to respective time phases obtained by subtracting a mask image imaged before the administration of contrast agent from an X-ray image of each time phase imaged after the administration of contrast agent are defined as DSA images.

However, blood constantly flows in blood vessels into which contrast agent is injected and inflow of the contrast agent is temporary. Therefore, an operator used to confirm regions of blood vessels and branch points of blood vessels, by imaging dying conditions of the contrast agent in the last several DSA images in his/her mind as afterimages so as to compare them with the dying condition of the latest DSA image.

If more contrast agent is injected into a patient over longer time, regions of blood vessels and branch points of blood vessels can be visualized for a longer time. However, this method undesirably increases burden on a patient.

Thus, novel technology to enable observation of a region of a blood vessel and a branch point of a blood vessel more satisfactorily than conventional technology (regardless of contrast agent amount) has been desired.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of an image processing device and an X-ray diagnostic apparatus according to embodiments of the present invention with reference to the drawings.

In general, according to one embodiment, an image processing device includes processing circuitry. The processing circuitry sequentially acquires image data of time-sequential DSA images of an object, and acquires a parameter value for each pixel based on temporal change of a pixel value of the each pixel corresponding to the same region of the object in the sequentially acquired image data of time-sequential DSA images. Further, the processing circuitry sequentially generates image data of parameter images in such a manner that identification information according to the parameter value is assigned to the each pixel corresponding to the same region of the object, each time image data of a DSA image of the latest time phase being acquired.

The First Embodiment

Figure 1:
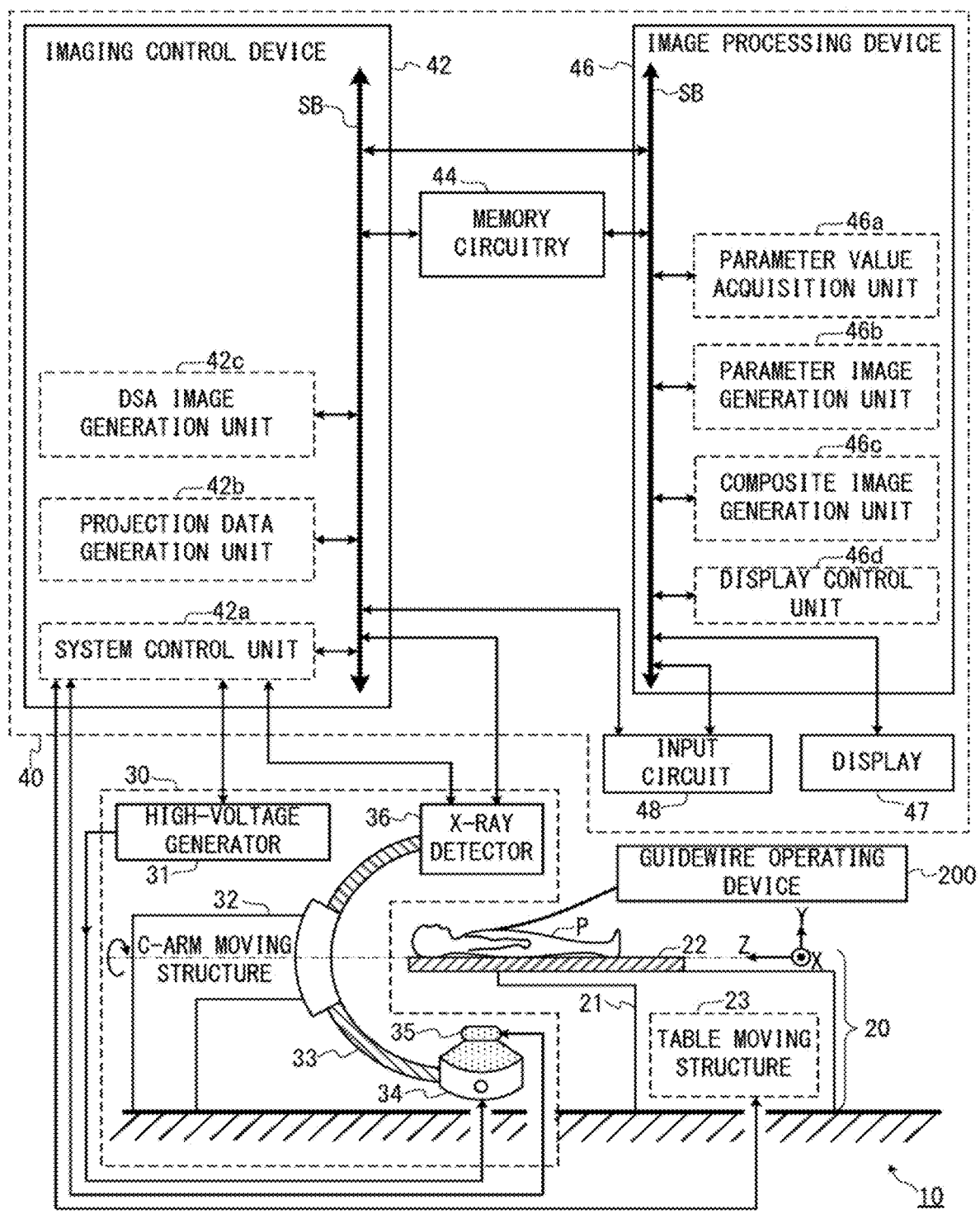
FIG. 1 is a block diagram showing an example of configuration of an X-ray diagnostic apparatus of the first embodiment of the present disclosure.

FIG. 1 is a block diagram showing an example of configuration of the X-ray diagnostic apparatus 10 of the first embodiment of the present disclosure. The hardware structure of the X-ray diagnostic apparatus 10 of each of the second to sixth embodiments described below is the same as the first embodiment. As an example here, components of the X-ray diagnostic apparatus 10 are classified into three groups: a bed device 20, an X-ray generating and detecting system 30, and a computing system 40.

Firstly, the bed device 20 includes a supporting platform 21, a table 22, and a table moving structure 23 disposed inside the supporting platform 21. An object P is loaded on the table 22. Although a guidewire operating device 200 is set on the object P as an example here, the guidewire operating device 200 will be explained in the sixth embodiment.

The supporting platform 21 supports the table 22 in such a manner that the table 22 can move in the horizontal direction (i.e. the z axis direction of the apparatus coordinate system). The table moving structure 23 positions an imaging region of the object P between an X-ray detector 36 and a diaphragm device 35 described below, by moving the table 22 in the Z axis direction of the apparatus coordinate system under control of a system control unit 42a of the computing system 40 described below.

As an example here, the above-described apparatus coordinate system, whose X axis, Y axis and Z axis are perpendicular to each other, is defined as follows.

First, the Y axis direction is defined as the vertical direction, and the table 22 is disposed in such a position that the direction of the normal line of its top surface accords with the Y axis direction. The horizontal moving direction of the table 22 is defined as the Z axis direction, and the table is disposed in such a manner that its longitudinal direction accords with the Z axis direction. The X axis direction is the direction perpendicular to these Y axis direction and Z axis direction.

Secondly, the X-ray generating and detecting system 30 includes a high-voltage generator 31, a C-arm moving structure 32, a C-arm 33, an X-ray tube 34, the diaphragm device 35, and the X-ray detector 36.

The C-arm 33 is an arm which supports the X-ray tube 34, the diaphragm device 35, and the X-ray detector 36. The X-ray detector 36 and the pair of the X-ray tube 34 and the diaphragm device 35 are arranged by the C-arm 33 so as to face each other with the object P interposed therebetween.

The C-arm moving structure 32 rotates and moves the C-arm 33 according to the imaging region under the control of the system control unit 42a.

The high-voltage generator 31 generates high voltage and supplies the X-ray tube 34 with the generated high voltage.

The X-ray tube 34 generates X-rays by consuming the high voltage supplied from the high-voltage generator 31.

The diaphragm device 35 narrows down an irradiation range of X-rays by, for example, sliding diaphragm blades so that X-rays are selectively irradiated on the imaging region of the object P, and controls the irradiation range by adjusting degree of opening of the diaphragm blades.

The X-ray detector 36 includes, for example, many of non-illustrated X-ray detection elements arrayed in a matrix for converting X-rays into electric signals. The X-ray detector 36 converts X-rays having passed through the object P into electric signals to accumulate these electric signals by using these X-ray detection elements, and outputs the accumulated electric signals to the projection data generation unit 42b described below.

Thirdly, the computing system 40 includes an imaging control device 42, memory circuitry 44, an image processing device 46, a display 47, and an input circuit 48.

The imaging control device 42 controls an imaging operation of the X-ray diagnostic apparatus 10. The imaging control device 42 includes the system control unit 42a, the projection data generation unit 42b, a DSA image generation unit 42c, and a system bus SB as communication wiring interconnecting these components.

The system control unit 42a controls the entirety of the X-ray diagnostic apparatus 10 in setting of imaging conditions, imaging operations, and display processing.

The projection data generation unit 42b generates projection data of X-ray images by using electric signals converted from the X-rays having passed through the object P by the X-ray detector 36. The projection data generation unit 42b stores the generated projection data in the memory circuitry 44.

The DSA image generation unit 42c acquires projection data of an X-ray image before administration of contrast agent (i.e. image data of a mask image) and projection data of X-ray images of respective time phases after the administration of contrast agent from the memory circuitry 44. Thereby, the DSA image generation unit 42c generates image data of DSA images of the respective time phases by calculating subtraction between the projection data of the mask image and the projection data of the X-ray image of each time phase after the administration of contrast agent. The DSA image generation unit 42c stores the image data of the DSA images in the memory circuitry 44.

The display 47 performs image display, display of setting screen of imaging conditions, display of setting screen of image processing conditions, etc. The above-described image display means display of the above-described X-ray images, DSA images, parameter images described below, and composite images obtained by composing these images.

The input circuit 48 includes a keyboard, a mouse MS (FIG. 5), operation buttons, etc. in order for a user to input various commands such as imaging conditions, image processing conditions, etc., and transfers the inputted contents to the system control unit 42a and the image processing device 46.

The image processing device 46 includes a parameter value acquisition unit 46a, a parameter image generation unit 46b, a composite image generation unit 46c, a display control unit 46d, and a system bus SB as communication wiring interconnecting these components.

The parameter value acquisition unit 46a acquires image data of time-sequential DSA images obtained by performing fluoroscopic imaging of the same object before and after the administration of contrast agent, from the memory circuitry 44.

Figure 2:
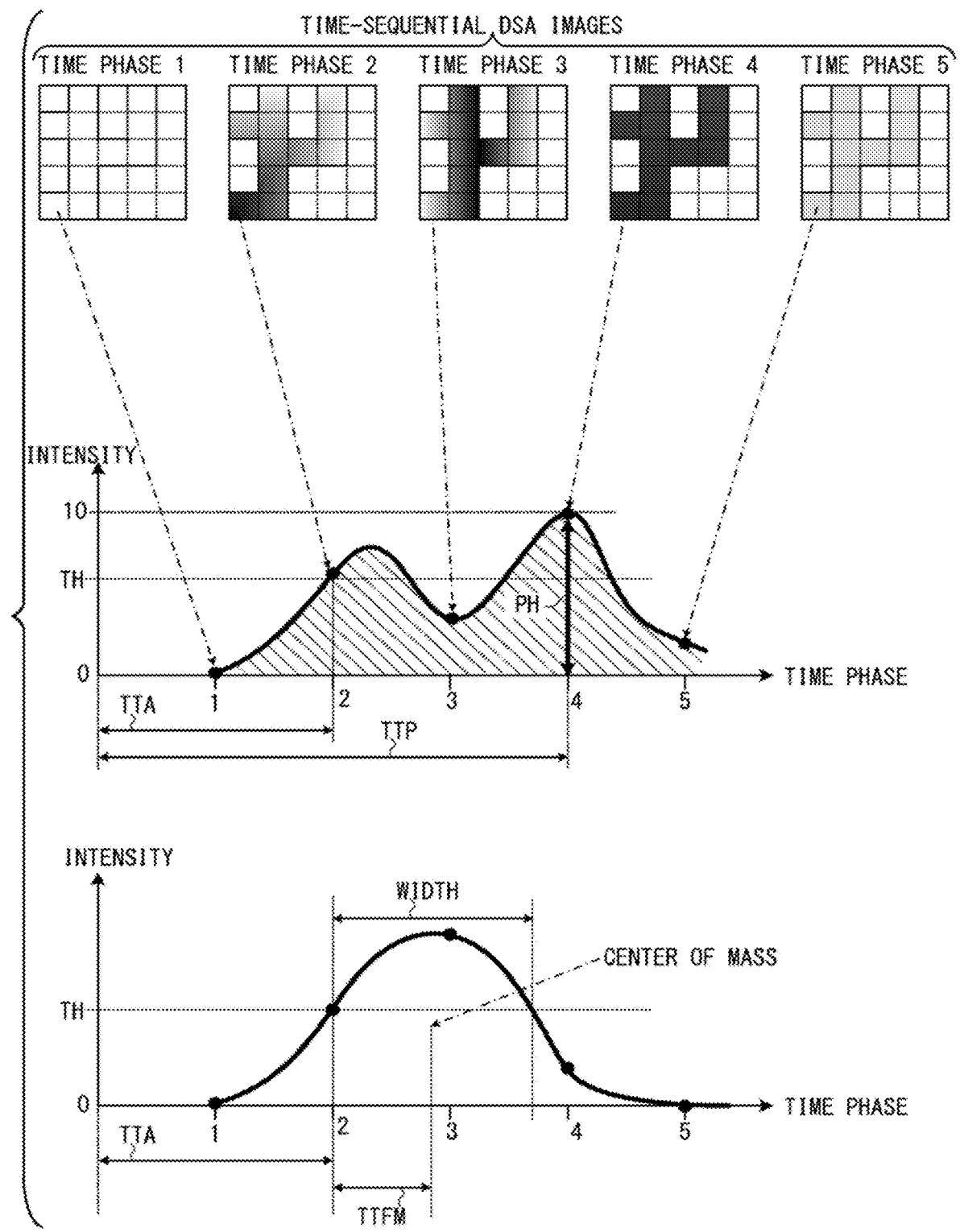
FIG. 2 is a schematic diagram showing a method of calculating temporal change of contrast agent concentration, as an example of a method of acquiring parameter values in a generation process of parameter images.

In addition, the parameter value acquisition unit 46a acquires parameter values of parametric imaging for each pixel, based on temporal change of pixel values of each pixel corresponding to the same region of the object in the image data of DSA images of the respective time phases (see FIG. 2).

The above-described parametric imaging means, for example, processing of forming a color image or gray-scale image from a single parameter or plural parameters. In a broad sense, the parametric imaging includes projection data of an X-ray image generated by the projection data generation unit 42b. This is because a pixel value of each pixel in projection data of an X-ray image indicates a value of X-ray transmissivity as a parameter.

In a narrow sense, the parametric imaging means processing of generating a color image by calculating parameter values except X-ray transmissivity for each pixel based on projection data of X-ray images. In the present embodiment, the parametric imaging in the narrow sense will be explained. In the following explanation, an image generated by the parametric imaging in the narrow sense is referred to as a parameter image.

The parameter image generation unit 46b generates image data of a parameter image, so that identification information in accordance with each parameter value is assigned to each pixel. It is enough that identification information is information indicative of different display aspects of each pixel depending on its parameter values. As the identification information, for example, monochrome gradation values, hue, gradation values of the same hue, luminance, transmissivity, and combination of these parameters may be used.

In the following, an example of a case where the parameter image generation unit 46b generates image data of parameter images so that hue (chromatic color) according to a parameter value is assigned to each pixel corresponding to the same region of the object P will be explained. In the following example, image data of a parameter image are image data in which each pixel has three pixel values for the respective three primary colors of red, green, and blue, for example. As an example here, it is assumed that image data of one parameter image are generated for a series of time-sequential DSA images.

The composite image generation unit 46c generates composite image data indicating a composite image between a DSA image and a parameter image.

The display control unit 46d makes the display 47 display composite images.

Since main characteristics of the X-ray diagnostic apparatus 10 are functions of the image processing device 46, methods of generating DSA images and parameter images necessary for detailed explanation of the functions the image processing device 46 will be explained first as follows.

FIG. 2 is a schematic diagram showing a method of calculating temporal change of contrast agent concentration, as an example of a method of acquiring parameter values in a generation process of parameter images. The top part of FIG. 2 shows DSA images of respective time phases, the middle part of FIG. 2 shows an example of temporal change of contrast agent concentration targeting one pixel. The bottom part of FIG. 2 shows another example of temporal change of contrast agent concentration targeting another pixel.

Since to include many parameters in one temporal change curve of contrast agent concentration makes it complicated, two temporal change curves are shown for convenience of explaining each parameter as shown in FIG. 2.

For example, consider a case where imaging is performed before and after administration of contrast agent by the X-ray diagnostic apparatus 10 so that projection data of six X-ray images for the same region of the same object P in the order of time t=0 before the administration, time t=1, 2, 3, 4, and 5 after the administration are generated by the projection data generation unit 42b. In this case, image data of five DSA images (subtraction images) corresponding to t=1, 2, 3, 4, and 5 can be obtained by subtracting the X-ray image at t=0 (mask image) from each of the five X-ray images after the administration (see the top part of FIG. 2).

Incidentally, in the top part of FIG. 2, t=1 is defined as the time phase 1, t=2 is defined as the time phase 2 (the same hereinafter). In addition, even if contrast agent is injected only once, plural local maximum values can be observed sometimes like the middle part of FIG. 2 in a region where plural blood vessels cross as an example.

Here, the parameter value acquisition unit 46a calculates temporal change of contrast agent concentration for each pixel by calculating pixel value change over the time phases from t=1 to t=5 for each pixel whose position is common to the five DSA images. The middle part of FIG. 2 shows an example of temporal change of contrast agent concentration targeting one pixel positioned at the bottom-left corner in each DSA image (whose pixel number is 5×5 in this example). In the middle part of FIG. 2, the vertical axis indicates contrast agent concentration (intensity of contrast agent) and the horizontal axis indicates time phase (elapsed time t). The same holds true for the bottom part of FIG. 2.

More specifically, the X-ray absorption rate of the contrast agent is higher than that of human tissues. Thus, exposure dose of an X-ray detection element corresponding to the position of the object P, where the contrast agent concentration is high, becomes lower, and the contrast agent in such a position of the object P is more darkly projected in an X-ray image than its peripheral regions.

Additionally, each pixel value of each DSA image is a difference value from the pixel value of the same position of the mask image (before administration of contrast agent). Thus, if one pixel of the same position is focused on and appropriate processing such as sign inversion etc. is performed on time phase change of the pixel values of this pixel, the result becomes equivalent to temporal change of the contrast agent concentration.

As parameters used for parameter images, TTP (Time To Peak), PH (Peak Height), and TTA (Time To Arrival) as shown in the middle part of FIG. 2, AUC (Area Under Curve) corresponding to square measure of the diagonally right down shadow region in the middle part of FIG. 2, WIDTH and TTFM (Time To First Moment) as shown in the bottom part of FIG. 2, etc. are included.

TTP indicates at which time phase contrast agent concentration reaches its peak.

PH indicates a peak value of contrast agent concentration.

AUC indicates a time integration value of contrast agent concentration from the first time phase to the final time phase of DSA images.

TTA is the time phase (clock time) when contrast agent concentration first exceeds a threshold value TH in the temporal change curve of contrast agent concentration.

WIDTH is a period (time interval) during which contrast agent concentration is higher than the threshold value TH.

TTFM is a period (time interval) from the timing of TTA (when contrast agent concentration first exceeds the threshold value TH) to the center of mass with respect to the time integration value of contrast agent concentration from the first time phase to the final time phase.

If DSA images, parameter images, and composite images are sequentially generated and their display is updated while performing fluoroscopic imaging on a real-time basis, a parameter by which color of pixels can be determined even in an intermediate time phase prior to end of the fluoroscopic imaging is desirable.

As such parameters, the above-described TTA, Wash-in, Wash-out, etc. are included. Wash-in is the first time phase (clock time) when a gradient (time differential value) reaches a positive predetermined value in the temporal change curve of contrast agent concentration. Wash-out is the first time phase (clock tire) when a gradient (time differential value) reaches a negative predetermined value in the temporal change curve of contrast agent concentration. Additionally, the time phase when AUC first exceeds a predetermined square measure is also a parameter by which color of pixels can be determined in an intermediate time phase prior to end of the fluoroscopic imaging.

As an example here, the parameter value acquisition unit 46a acquires TTA as a parameter value for each pixel, based on temporal change of contrast agent concentration. Note that as a parameter of a parameter image, the above-described parameters such as TTP, PH, AUC, Wash-in, Wash-out, etc. and other parameters may be used.

In the case of TTP as an example, to be exact, the peak time phase cannot be determined unless the fluoroscopic imaging is completed. This is because there is a possibility that contrast agent concentration reaches its peak at the final time phase. However, in the case of a post-process performed after completion of imaging of X-ray images of all the time phases after administration of contrast agent, values of TTP can be determined-without any problem. For the above reason, when images are sequentially updated and displayed while performing fluoroscopic imaging on a real-time basis, TTP may be determined before completion of imaging of all the time phases based on the peak time phase within the range up to that time in a temporal change curve of contrast agent concentration, for example.

Figure 3:
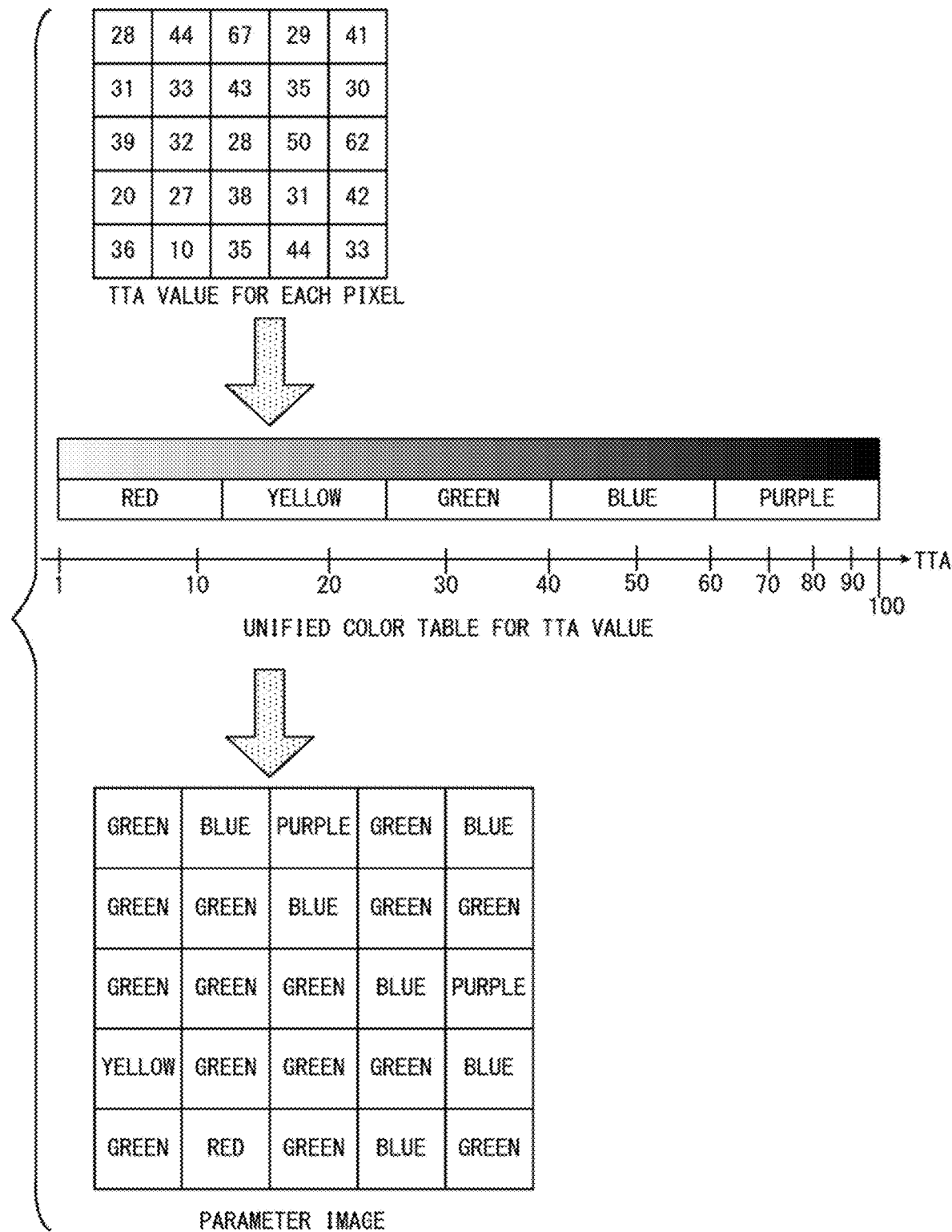
FIG. 3 is a schematic diagram showing an example of a method of generating a parameter image whose parameter is TTA.

FIG. 3 is a schematic diagram showing an example of a method of generating a parameter image whose parameter is TTA. The top part of FIG. 3 shows an example of calculated TTA values for each pixel whose position is common to all the frames of DSA images, under the premise that pixel number is 5×5 as an example.

The middle part of FIG. 3 shows an example of a color table for TTA stored in the parameter image generation unit 46b. As an example here, a case where one hundred frames are imaged after administration of contrast agent (i.e. DSA images from time phase 1 to time phase 100 are generated) is shown. In addition, as an example here, it is assumed that the color table used for generating parameter images is unified (fixed) regardless of the number of DSA images (number of time phases)

More specifically, in the first embodiment as an example, a case where each composite image between a DSA image of the latest time phase and a parameter image corresponding to the latest time phase is updated and displayed while performing fluoroscopic imaging on a real-time basis to acquire sequentially generated DSA images is considered.

In other words, immediately after imaging the X-ray image of the third time phase posterior to administration of contrast agent, the parameter image corresponding to the third time phase is generated based on the three DSA images of the first to third time phases and the unified color table shown in the middle part of FIG. 3. Then, the display control unit 46d makes the display 47 display the composite image between the DSA image of the third time phase and the parameter image corresponding to the third time phase.

Afterward, immediately after imaging the X-ray image of the fourth time phase, the parameter image corresponding to the fourth time phase is generated based on the four DSA images of the first to fourth time phases and the unified color table, and the composite image between the DSA image of the fourth time phase and the parameter image corresponding to the fourth time phase is displayed. Hereinafter, the composite image is updated and displayed in the same way.

As described above, (a) generation of a DSA image of the latest time phase and a parameter image corresponding to the latest time phase and (b) generation and display of a composite image between these two images are sequentially repeated on a real-time basis.

Note that the present embodiment is not limited to an aspect of performing image display processing while performing fluoroscopic imaging on a real-time basis. The above-described processing may be performed as a post-process after completing imaging of X-ray images of all the time phases posterior to administration of contrast agent.

Since imaging time and frame number are generally determined before start of fluoroscopic imaging, it is enough that the parameter image generation unit 46b determines the color table depending on the frame number. The reason of unifying the color table is because it becomes unintelligible unless color of each pixel is assigned only depending on parameter values. For example, consider one pixel of a certain position, whose contrast agent concentration exceeds a threshold value at the first time phase, and whose parameter values of TTA are constant after the first time phase. If different colors are assigned to this pixel for respective time phases after the first time phase, the logic of generating a parameter image becomes unintelligible.

Although the processing regarding parameter images is based on update and display, the parameter image corresponding to the final time phase becomes the same as the parameter image corresponding the second-to-final time phase if TTA of every pixel appears before the final time phase as an example.

As an example in FIG. 3, one of red, yellow, green, blue, and purple is assigned to each pixel in the ascending order of a TTA value of a pixel. Although a method of assigning color is arbitrary, it is desirable that chromatic color is assigned to plural pixels in the color assignment. This is because it is difficult to distinguish a blood vessel region from its surrounding regions in gray-scale display.

The color table is indicated as a bar in the horizontal direction for convenience in FIG. 3. However, the color table may be practically stored as a color bar composed of chromatic colors. The parameter image generation unit 46b may store the color table as table data in which a set of a red value, a green value, and a blue value as three primary colors in a predetermined bit notation is given for each of TTA values.

The bottom part of FIG. 3 shows color of each pixel defined by a TTA value of each pixel in the top part of FIG. 3 and the color table in the middle part of FIG. 3. In other words, a parameter image of TTA is an image whose pixels are displayed with color shown by the bottom part of FIG. 3.

Next, a method of generating a composite image between a DSA image and a parameter image will be explained.

A DSA image is an achromatic gray-scale image, and a parameter image is a chromatic color image based on pixel values of DSA images. Here, as long as a parameter image is generated based on DSA images of plural time phases, each of DSA images is equal to a parameter image (derived from these DSA images) in size and indicates the same region of the same object as the parameter image. Thus, as to composition, it is enough to position so that four corners of a DSA image are aligned with four corners of a parameter image, as an example. Accordingly, problem of positional displacement never occurs.

Here, the above-described composition means to generate one composite image so that information of plural original images is included in the composite image. Composition is assumed to be a broader concept including at least an average image of both images, insertion (to be explained in the third example below), etc. Examples of composition methods are as follows.

Firstly, a simple average of a DSA image and a parameter image may be treated as a composite image. For example, consider a case where three pixel values of each pixel are indicated by luminance level of each of red, green, and blue as three primary colors and the luminance level is composed of 256 stages ranging from 0 to 255. As an example, the pixel values of the pixel β positioned at the bottom-left corner of the parameter image corresponding time phase α are assumed to be (255, 0, 0) indicative of pure red color.

In addition, the pixel values of the pixel β' positioned at the bottom-left corner of the DSA image corresponding time phase α are assumed to be (128, 128, 128). Since a DSA image is a gray-scale image, three pixel values of red, green, and blue of each pixel of a DSA image are equal to each other. In this case, the pixel values of the pixel β" positioned at the bottom-left corner of the composite image are (192, 64, 64). By performing such processing on all the pixels, image data of a composite image can be obtained.

Secondly, a weighted average of a DSA image and a parameter image may be treated as a composite image. It is assumed that weight coefficients can be freely set via the input circuit 48. For example, consider a case where a weighted average between the above-described pixels β and β' positioned at the bottom-left corner is taken so that weight of the parameter image is larger than weight of the DSA image by the ratio of three to one.

In this case, since $(255\times3+128\times1)/(3+1)=223.25$, and $(0\times3+128\times1)/(3+1)=32$, the pixel values of the pixel β" positioned at the bottom-left corner of the composite image are given by (223, 32, 32).

Thirdly, a composite image may be generated inserting a blood vessel into a parameter image. The above-described blood vessel image may be generated by extracting only blood vessel regions from a DSA image, and pixel values of the blood vessel image are zero except the blood vessel regions as an example. Insertion in this third example means to use pixel values of the blood vessel image as to pixels whose pixel values are not zero in the blood vessel image and to use pixel values of the parameter image for the rest of the pixels, after positional alignment of both images. In this case, the chromatic parameter image, in which the achromatic blood vessel image is partially mixed, is the composite image to be generated.

As an example in the first embodiment, the weighted average of the second example is used for composite images.

Figure 4:
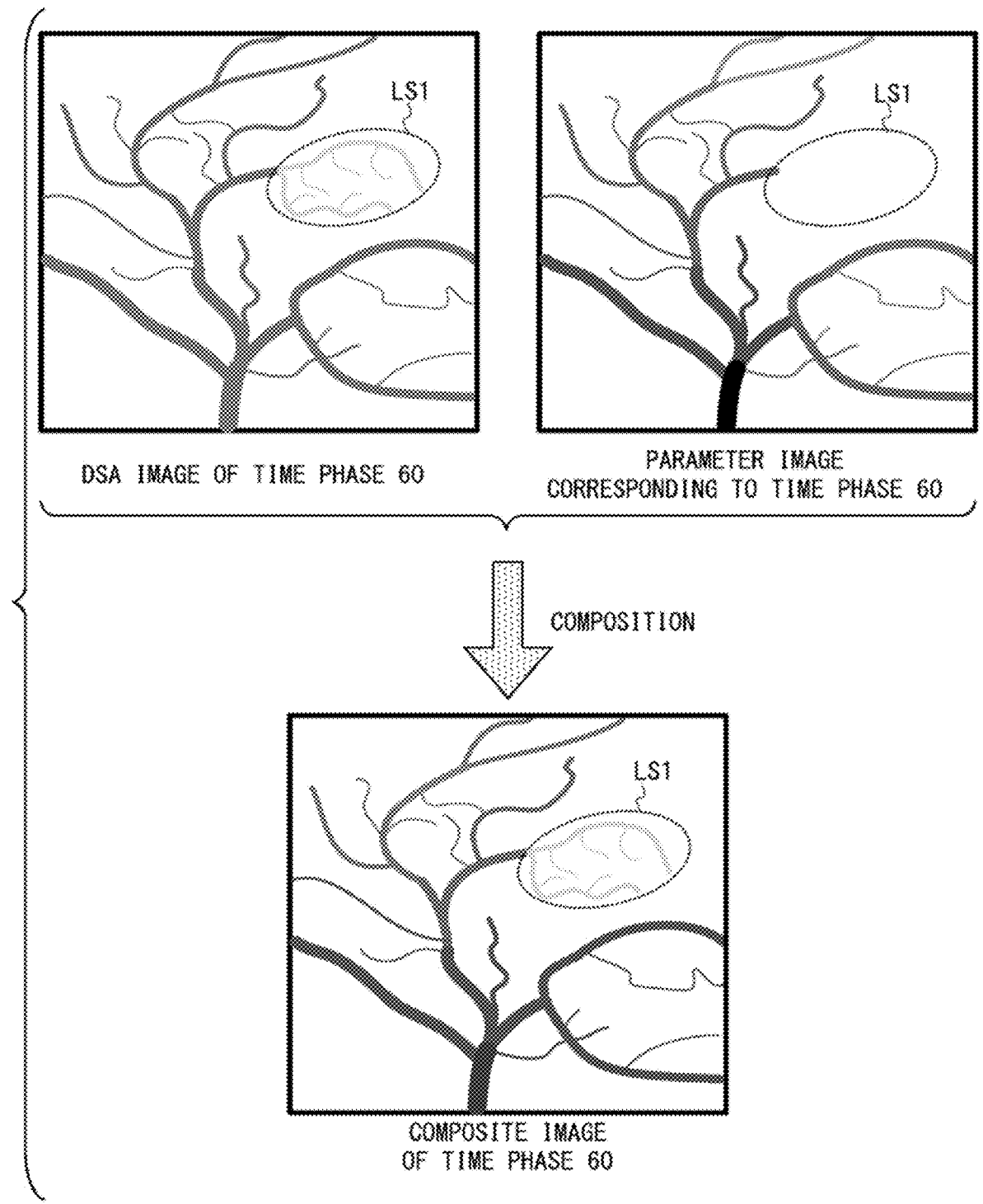
FIG. 4 is a schematic diagram showing an example of a composite image generated by calculating a weighted average of a DSA image and a parameter image, both of which correspond to a common time phase.

FIG. 4 is a schematic diagram showing an example of each composite image generated by calculating a weighted average of a DSA image and a parameter image, both of which correspond to the same time phase. The left side of the upper part of FIG. 4 shows an example of a DSA image of the time phase 60. The right side of the upper part of FIG. 4 shows an example of a parameter image generated based on 60 DSA images of the time phases 1 to 60. The lower part of FIG. 4 shows an example of a composite image between these two images shown in the upper part of FIG. 4.

In the upper part and lower part of FIG. 4, the region surrounded with an elliptical broken line is a candidate lesion region LS1 (i.e. a low perfusion region) where blood flow amount is small. The above-described candidate lesion region is assumed to mean both of a lesion region and a region which cannot be determined to be a lesion region or a normal region. A lesion region means, for example, a coarctation region where blood vessels are narrowed, an occlusion region where a blood vessel is occluded, and so on.

Since a DSA image is a gray-scale image as shown in the left side of the upper part of FIG. 4, it is difficult to judge the difference between the candidate lesion region LS1 and its peripheral normal regions.

The parameter image shown in the right side of the upper part of FIG. 4 is actually displayed as a color image composed of various chromatic colors according to the color map in the middle part of FIG. 3. However, for convenience here, it is drawn in FIG. 4 as a gray-scale schematic image so that a pixel of a smaller TTA value is more blackly indicated as an example. In the example of this schematic image, the candidate lesion region LS1 cannot be distinguished as blood vessels in the parameter image whose parameter is TTA as an example.

As reasons why the candidate lesion region LS1 cannot be distinguished as blood vessels, the following cases are possible, for example.

Firstly, since the candidate lesion region LS1 is a low perfusion region, a case where contrast agent concentration of every pixel in the candidate lesion region LS1 does not exceed the threshold value TH up to the time phase 60 is possible.

Secondly, even if contrast agent concentration of at least one pixel in the candidate lesion region LS1 exceeds the threshold value TH until the time phase 60, the candidate lesion region LS1 may become undistinguishable in the following case. When a PH value (dose having passed through the object P and detected by the X-ray detector 36) as a factor of determining a transmissivity value is low and this causes transmissivity of the candidate lesion region LS1 to become higher than other color regions, the candidate lesion region LS1 is undistinguishable. This is because transmissivity is also included in the factors that determine color of each pixel in color representation of parameter values.

In the composite image shown in the lower part of FIG. 4, chroma of this composite image becomes lower than that of the parameter image, by the average processing between this composite image and the gray-scale DSA image. Despite the lowered chroma, blood vessels in normal regions in this composite image are displayed by various chromatic colors. Incidentally, chroma of the composite image can be increased, by setting the weight coefficient of each parameter image to a value higher than the weight coefficient of each DSA image in the weighted average processing.

Meanwhile, in the composite image, blood vessels in the candidate lesion region LS1 are reflected based on gray-scale display by blood flow information included in the DSA image. This is because every pixel value in the candidate lesion region LS1 of the parameter image is zero and thus the candidate lesion region LS1 is not distinguished as a blood vessel region in the example of FIG. 4.

Whereas the candidate lesion region LS1 is lightly displayed under gray-scale, the surrounding normal regions are clearly displayed with various chromatic colors, and consequently a user can easily distinguish between the region LS1 and the normal region. Accordingly, in the composite image, blood vessels in the candidate lesion region LS1 become more distinguishable from the surrounding normal regions.

Here, though the display control unit 46*d* can display the composite images sequentially generated on a real-time basis on the display 47 in time-sequential order like a moving picture, aspects of image display are not limited to automatic display in time-sequential order. In the case of a post-process as an example, the display control unit 46*d* can display the composite image on the display 47 according to a user's operation.

Figure 5:
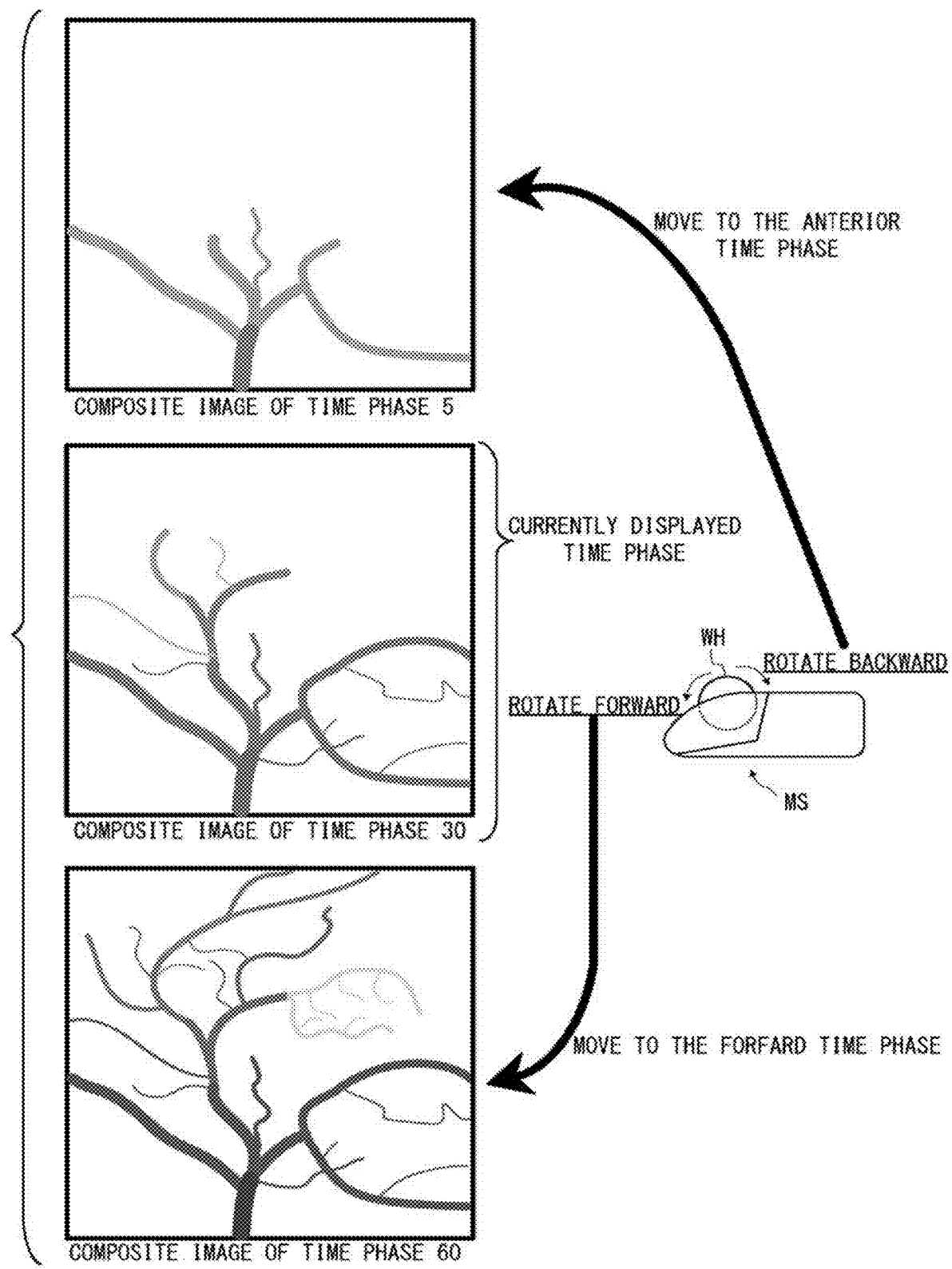
FIG. 5 is a schematic diagram showing an example of a method of displaying composite images in accordance with a user's operation, as a post-process.

FIG. 5 is a schematic diagram showing an example of a method of displaying composite images according to a user's operation, as a post-process. In the left side of FIG. 5, the top part is an example of a composite image of the time phase 5, the middle part is an example of a composite image of the time phase 30, and the bottom part is an example of a composite image of the time phase 60.

As an example here, it is assumed that the composite image of the time phase 30 is currently displayed on the display 47 as a post-process. The display control unit 46d advances or puts back the time phase of the composite image to be displayed on the display 47 in time-sequential order, according to rotation of the mouse wheel WH of the mouse MS shown in the middle part of the right side of FIG. 5.

In other words, a user can switch the displayed composite image from the currently displayed one to another one whose time phase is more advanced than the currently displayed one, by rotating the mouse wheel WH forward. In this case, displayed composite images are switched to the one of time phase 31, the one of time phase 32, the one of time phase 33, . . . , and display of composite images is once fixed at the composite image of the time phase corresponding to the timing when a user stopped moving the mouse wheel WH.

Similarly, a user can switch the displayed composite image from the currently displayed one to another one whose time phase is prior to the currently displayed one, by rotating the mouse wheel WI backward.

In addition, the display control unit 46d can display DSA images of the respective time phases and each parameter image according to a user's operation like FIG. 5, in addition to the above-described display of composite images.

Figure 6:
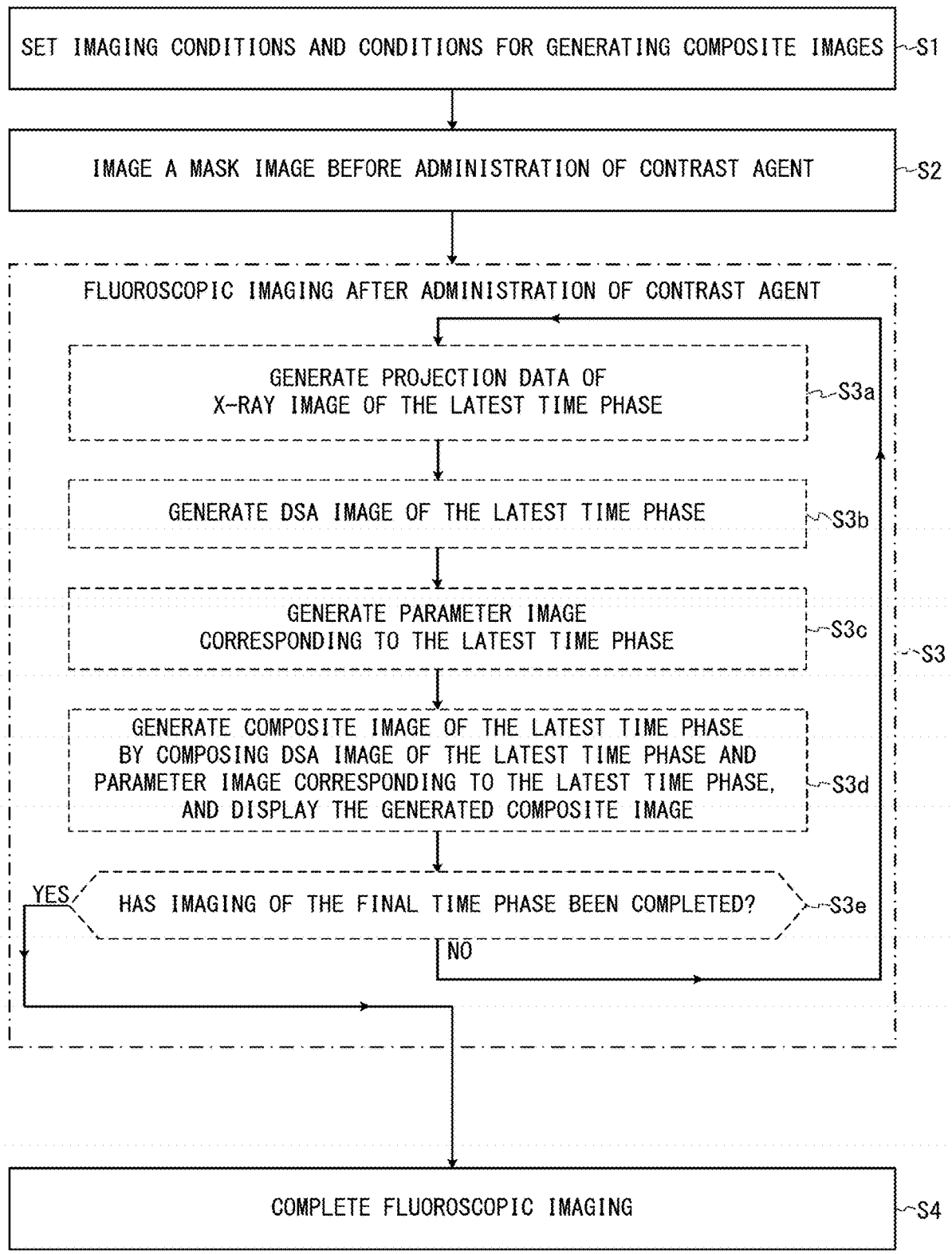
FIG. 6 is a flowchart showing an example of an operation of the X-ray diagnostic apparatus of the first embodiment, when composite images are updated and displayed to follow fluoroscopic imaging performed on a real-time basis.

FIG. 6 is a flowchart showing an example of an operation of the X-ray diagnostic apparatus 10 of the first embodiment, when composite images are updated and displayed to follow fluoroscopic imaging performed on a real-time basis. Hereinafter, according to the step numbers in the flowchart shown in FIG. 6, an operation of the X-ray diagnostic apparatus 10 will be explained by referring to the above-described FIG. 1 to FIG. 5 as required.

[Step S1] Some of imaging conditions such as a tube current, a tube voltage, imaging time, imaging interval after administration of contrast agent, frame number after administration of contrast agent, etc. and conditions for generating composite images are inputted by a user via the input circuit 48. The above-described conditions for generating composite images mean what is used as a parameter of parameter images, weight coefficients in weighted average processing between a parameter image and a DSA image, etc.

The system control unit 42a (FIG. 1) determines all the imaging conditions according to the inputted imaging conditions. In addition, the parameter value acquisition unit 46a determines the parameter (TTA in this example) according to the inputted conditions, and the parameter image generation unit 46b determines the color map unified over all the time phases according to the determined parameter and the imaging conditions such as frame number etc.

As to the color map, various color maps according to the number of time phase and type of parameter may be preliminarily stored in the memory circuitry 44 before imaging, so that the parameter image generation unit 46b can select and read out the color map whose conditions are closest to the determined imaging conditions and the determined conditions for generating composite images out of all the preliminarily stored color maps.

Afterward, the processing proceeds to the Step S2.

[Step S2] First, the positions of the table 22, the C-arm 33, etc. are fixed, and thereby the imaging region of the object P is fixed to the same region. Then, before administration of contrast agent, projection data of an X-ray image is generated for the imaging region of the object P by a conventionally known operation.

Specifically, the high-voltage generator 31 supplies the X-ray tube 34 with high voltage under the control of the system control unit 42a, the X-ray tube 34 generates X-rays, and the irradiation region of X-rays onto the object P is controlled by the diaphragm device 35.

The X-ray detector 36 converts X-rays having passed through the object P into electric signals, and outputs the electric signals to the projection data generation unit 42b. The projection data generation unit 42b generates projection data of an X-ray image from the inputted electric signals, and stores the projection data in the memory circuitry 44. In this manner, projection data (i.e. image data of a mask image) is generated for the region of interest of the object P before the administration of contrast agent, so that luminance of each pixel becomes the level according to dose of the corresponding X-ray detection element (not shown) of the X-ray detector 36.

Although plural X-ray images are necessary after the administration of contrast agent to be described below, the X-ray image before the administration of contrast agent may be imaged only once or it may be an average of plural X-ray images imaged before the administration of contrast agent.

Afterward, the processing proceeds to the Step S3.

[Step S3] While the positions of the table 22, the C-arm 33, etc. are fixed, contrast agent is administered to the object P by remote control of a non-illustrated contrast agent administration device and then fluoroscopic imaging after the administration of contrast agent is performed on the same imaging region as the Step S2 according to the following detailed flow from the Steps S3a to S3e.

In the Step S3a, each component of the X-ray diagnostic apparatus 10 operates so as to generate projection data of one X-ray image. In other words, projection data of an X-ray image of the latest time phase are generated. Although the processing is divided into the Steps S3a to S3e in order to simplify the explanation here, this is only an example. In other words, the imaging operation of the Step S3a is performed independently of the computing processing of the Steps S3b to S3e according to the imaging interval determined in the Step S1, regardless of progress status of generation of parameter images and composite images and display processing in the Steps S3b to S3d.

Afterward, the processing proceeds to the Step S3b.

In the Step S3b, the DSA image generation unit 42c generates image data of a DSA image of the latest time phase based on difference between the image data of the mask image and the projection data of the X-ray image of the latest time phase generated in the Step S3a, and stores the generated image data in the memory circuitry 44.

Afterward, the processing proceeds to the Step S3c.

In the Step S3c, each of the parameter value acquisition unit 46a and the composite image generation unit 46 acquires the image data of the DSA image of the latest time phase from the memory circuitry 44. Each of the parameter value acquisition unit 46a and the composite image generation unit 46 stores the image data of all the DSA images acquired up to the immediately prior cycle and the image data of the DSA image of the latest time phase acquired in this cycle, until at least fluoroscopic imaging is completed.

The parameter value acquisition unit 46a calculates change of contrast agent concentration over the time phases up to the latest time phase for each pixel, based on the image data of the respective DSA images from the first time phase to the latest time phase after the administration of contrast agent (see FIG. 2).

Next, the parameter value acquisition unit 46a determines a TTA value as a parameter for each pixel based on the change of contrast agent concentration over the time phases, and outputs the determined TTA values to the parameter image generation unit 46b. TTA values of many pixels are not determined in earlier time phases, and it is possible that TTA values of some pixels are not determined even in the final time phase.

Afterward, the parameter image generation unit 46b generates image data of the parameter image corresponding to the latest time phase, based on the TTA value of each pixel inputted from the parameter value acquisition unit 46a and the color map (see FIG. 3).

The parameter image generation unit 46b outputs the image data of the parameter image corresponding to the latest time phase to the composite image generation unit 46c, and stores the image data of the parameter image corresponding to the latest time phase in the memory circuitry 44. Incidentally, as to each pixel whose TTA value is not determined, for example, its pixel values may be uniformly treated as (0, 0, 0) indicating a red pixel value, a green pixel value, and a blue pixel value are all zero.

Afterward, the processing proceeds to the Step S3d.

In the Step S3d, the composite image generation unit 46c generates the image data of the composite image of the latest time phase by composing the DSA image of the latest time phase and the parameter image corresponding to the latest time phase, according to the weight coefficients determined in the Step S1 (see the lower part of FIG. 4). The composite image generation unit 46c outputs the image data of the composite image of the latest time phase to the display control unit 46d, and stores the image data of the composite image of the latest time phase in the memory circuitry 44.

The display control unit 46d outputs the image data of the composite image of the latest time phase to the display 47, and makes the display 47 switch the displayed image to the composite image of the latest time phase.

Afterward, the processing proceeds to the Step S3e.

In the Step S3e, whether imaging of the X-ray image of the final time phase is completed or not is determined. If it is not completed, the processing returns to the Step S3a. If it is completed, the processing proceeds to the Step S4.

In other words, the composite image of the latest time phase is updated and displayed on the display 47, by repeating the processing of the Steps S3a to S3e by the number of times equal to the frame number of the X-ray images after the administration of contrast agent determined in the Step S1 (i.e. the number of time phases of DSA images).

Incidentally, an image displayed on the display 47 at an arbitrary time is not limited to only a composite image. For example, three images including a DSA image, a parameter image, and a composite image may be displayed in parallel on the display 47 at an arbitrary time. In other words, the display control unit 46d may update three images including a DSA image of the latest time phase, a parameter image corresponding to the latest time phase, and a composite image of the latest time phase, so as to display these updated three images on the display 47.

[Step S4] When the processing reaches this Step S4, imaging of the final time phase has been completed and the composite image of the final time phase is displayed. The system control unit 42a controls each component of the X-ray diagnostic apparatus 10 so as to make the X-ray diagnostic apparatus 10 stop operation of fluoroscopic imaging.

The foregoing is the explanation of the flow of FIG. 6. Note that generation of parameter images and composite images and display of these images may be performed as a post-process after completion of fluoroscopic imaging, instead of the above-described real-time processing (the same holds true for the second to the fifth embodiments to be described below).

In the case of a post-process, each of the parameter value acquisition unit 46a and the composite image generation unit 46c collectively acquires the image data of the DSA images of all the time phases from the memory circuitry 44, the parameter value acquisition unit 46a and the parameter image generation unit 46b generate the parameter images of all the time phases in the above-described manner, and the composite image generation unit 46c generates the composite images of all the time phases in the above-described manner. In this case, generation of the parameter images of all the time phases and the composite images of all the time phases and time-sequential display of these images are repeated, each time a user changes at least one of image processing conditions such as weight coefficients etc.

The foregoing is the explanation of the operation of the first embodiment. Hereinafter, the difference between conventional technology and the first embodiment will be explained.

Idea of superimposing a parameter image, in which temporal information on blood flow is reflected, on another image such as a DSA image etc. does not exist in conventional technology. If a superimposed image of a past image and a real-time fluoroscopic image is generated, the past image does not depict exactly the same object region as the real-time fluoroscopic image and thus both images do not completely match each other in positioning.

By contrast, in the first embodiment, two types of image data having mutually different information are generated from unified original image data of the same region of the object P including a mask image and X-ray images after the administration of contrast agent. In other words, DSA images indicative of region information on blood vessels and parameter images indicative of temporal information of blood flow are generated, and a composite image is generated by composing a DSA image and a parameter image.

As long as data of original images for generating each composite image are common, a problem of positional displacement does not occur as to image composition processing. In other words, a blood vessel region of a gray-scale DSA image and a blood vessel region of a parameter image perfectly matches each other in the composite image of both images. Thus, a case where blood flow information is partially lost by image composition processing never occurs.

As explained in FIG. 4, while the candidate lesion region LS1 is lightly displayed under gray-scale, the surrounding normal regions are clearly displayed with various chromatic colors, and consequently a user can easily distinguish between the region LS1 and the normal region. Accordingly, in the composite image, blood vessels in the candidate lesion region LS1 become more distinguishable from the surrounding normal regions. Additionally, temporal information on blood flow can be observed by change in chromatic color in each composite image, in a manner similar to that of each parameter image.

Moreover, when TTA is selected as a parameter value as an example, calculation of parameter values and generation of parameter images and composite images can be performed on a real-time basis, and thus a candidate lesion region LS1 can be specified in real-time while performing fluoroscopic imaging like FIG. 6. In the case of a post-process, time-sequential composite images can be displayed in time-series order like a moving picture based on projection data which are available after completion of imaging before and after administration of contrast agent. Further, in the case of a post-process, the above composite images can be displayed like a still image by stopping at a certain time phase.

In addition, in the case of a post-process, a user can advance or put back the time phase of the currently displayed composite image (and/or a DSA image etc.), by rotational operation of the mouse wheel WH as an example (see FIG. 5)

To be precise, the peak time of contrast agent concentration cannot be determined in the case of TTA, unless fluoroscopic imaging is completed. However, when contrast agent concentration of a pixel of an arbitrary position exceeds the threshold value TH at a certain time phase, the color of this pixel can be determined after the peak time phase in the case of TTA. Accordingly, the method of updating and displaying composite images in the first embodiment in which TTA is used as a parameter can be easily applied to fluoroscopic imaging on a real-time basis.

As mentioned above, even if a blood vessel can be observed only in a limited short span in time-sequential DSA images due to transient inflow of contrast agent, a region of a blood vessel and a branch point of a blood vessel can be more satisfactorily observed in the first embodiment without increasing contrast agent amount than conventional technology. As a result, convenience for a user is highly improved, and burden on a patient is potentially reduced.

The Second Embodiment

The second to fifth embodiments are similar to the first embodiment, except the difference in which of DSA images and/or parameter images are used as original images for generating a composite image of the latest time phase. In the second to the fifth embodiments, only different points from other embodiments will be explained.

Out of two original images for generating each composite image in the second embodiment, one is a parameter image corresponding to the latest time phase like the first embodiment, whereas the other is unified to a DSA image of a selected time phase.

Figure 7:
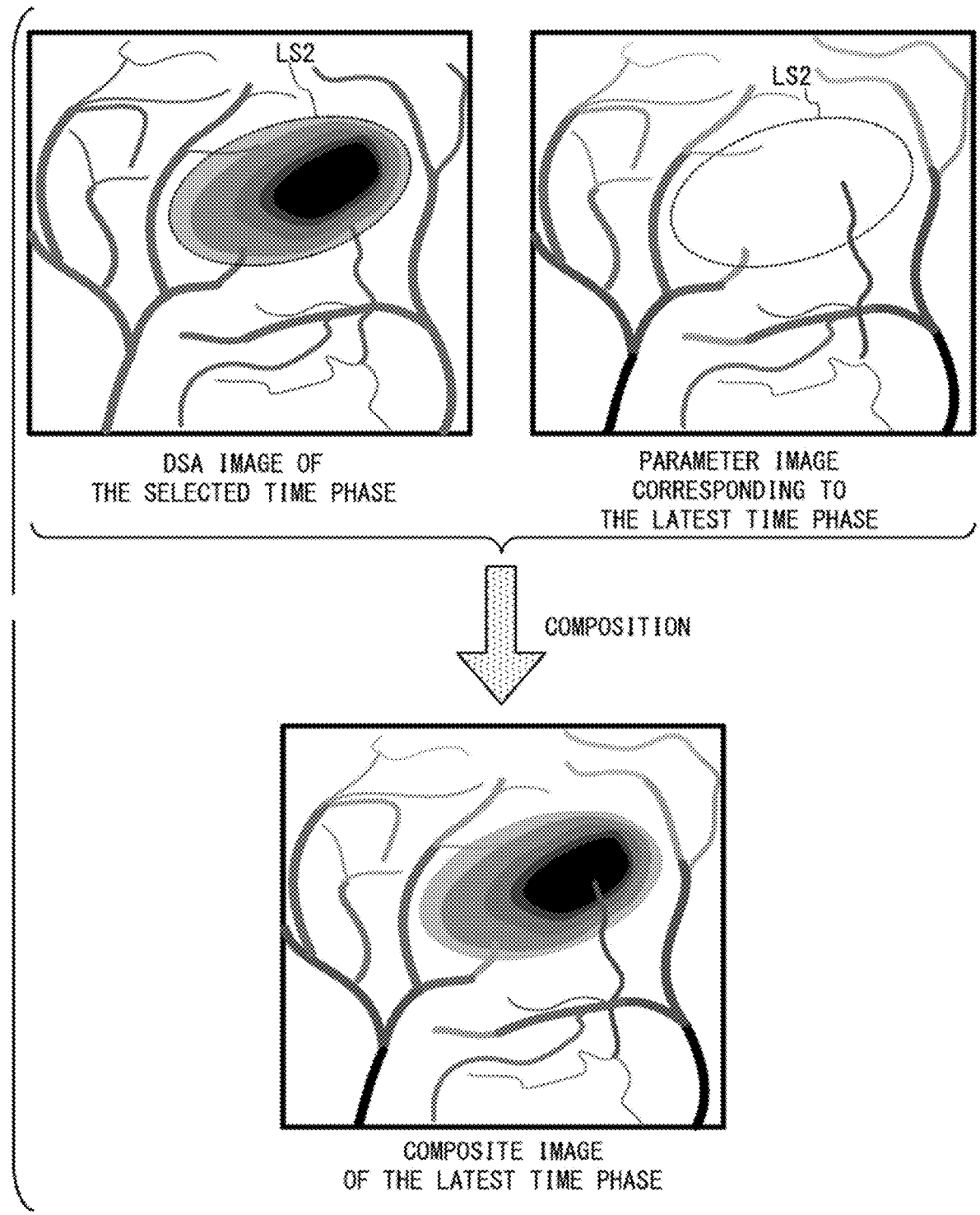
FIG. 7 is a schematic diagram showing an example of a composite image of the latest time phase generated by composing a DSA image of a selected time phase and the parameter image corresponding to the latest time phase, in the second embodiment.

FIG. 7 is a schematic diagram showing an example of a composite image of the latest time phase, which is generated by composing a DSA image of a selected time phase and a parameter image corresponding to the latest time phase in the second embodiment. The left side of the upper part of FIG. 7 shows an example of a DSA image of a selected time phase, and the right side of the upper part of FIG. 7 shows an example of a parameter image corresponding to the latest time phase. The lower part of FIG. 7 shows an example of a composite image of these two images.

In the upper part and lower part of FIG. 7, the region surrounded by an elliptical broken line is a candidate lesion region LS2 (tumor in this example). As shown in the left side of the upper part of FIG. 7, the selected DSA image is an image in which the candidate lesion region LS2 is more distinguishably depicted (darkly projected) than its previous time phase and its next time phase.

The parameter image in the right side of the upper side of FIG. 7 is drawn as a gray-scale schematic diagram for convenience like FIG. 4 so that a pixel with a lower TTA value is more blackly displayed. In the example of this schematic diagram, it is difficult to distinguish which region is the candidate lesion region LS2. However, actually displayed parameter image is a color image whose parameter is TTA as an example, and temporal change of blood flow around the candidate lesion region LS2 can be visually distinguishable by change in chromatic color.

The position of the candidate lesion region LS2 can be visually recognized in the composite image as shown in the lower part of FIG. 7, because blood flow information included in the DSA image as one of the original images is clearly reflected on the composite image. In addition, temporal change of blood flow is indicated as change in chromatic color in each composite image due to effect of taking in a parameter image as one of two original images. Therefore, in each composite image, a blood vessel flowing into the candidate lesion region LS2 and a blood vessel flowing out of the candidate lesion region LS2 can be distinguished by change in chromatic color.

In the case of a post-process, a user can select the DSA image of the time phase, at which the candidate lesion region LS2 such as a tumor etc. is most deeply projected, via the input circuit 48.

When composite images are updated and displayed while performing fluoroscopic imaging on a real-time basis, each component of the X-ray diagnostic apparatus 10 operates, for example, as follows.

Until a DSA image of one time phase is selected by a user, the display control unit 46d makes the display 47 update and display a DSA image of the latest time phase, a parameter image corresponding to the latest time phase, and a composite image in a manner similar to the first embodiment. After a DSA image of one time phase is selected by a user, the composite image generation unit 46c fixes one of two original images for generating each composite image to the selected DSA image and sequentially generates image data of composite images in a similar manner. More specifically, this operation becomes like the flow shown in FIG. 8.

Figure 8:
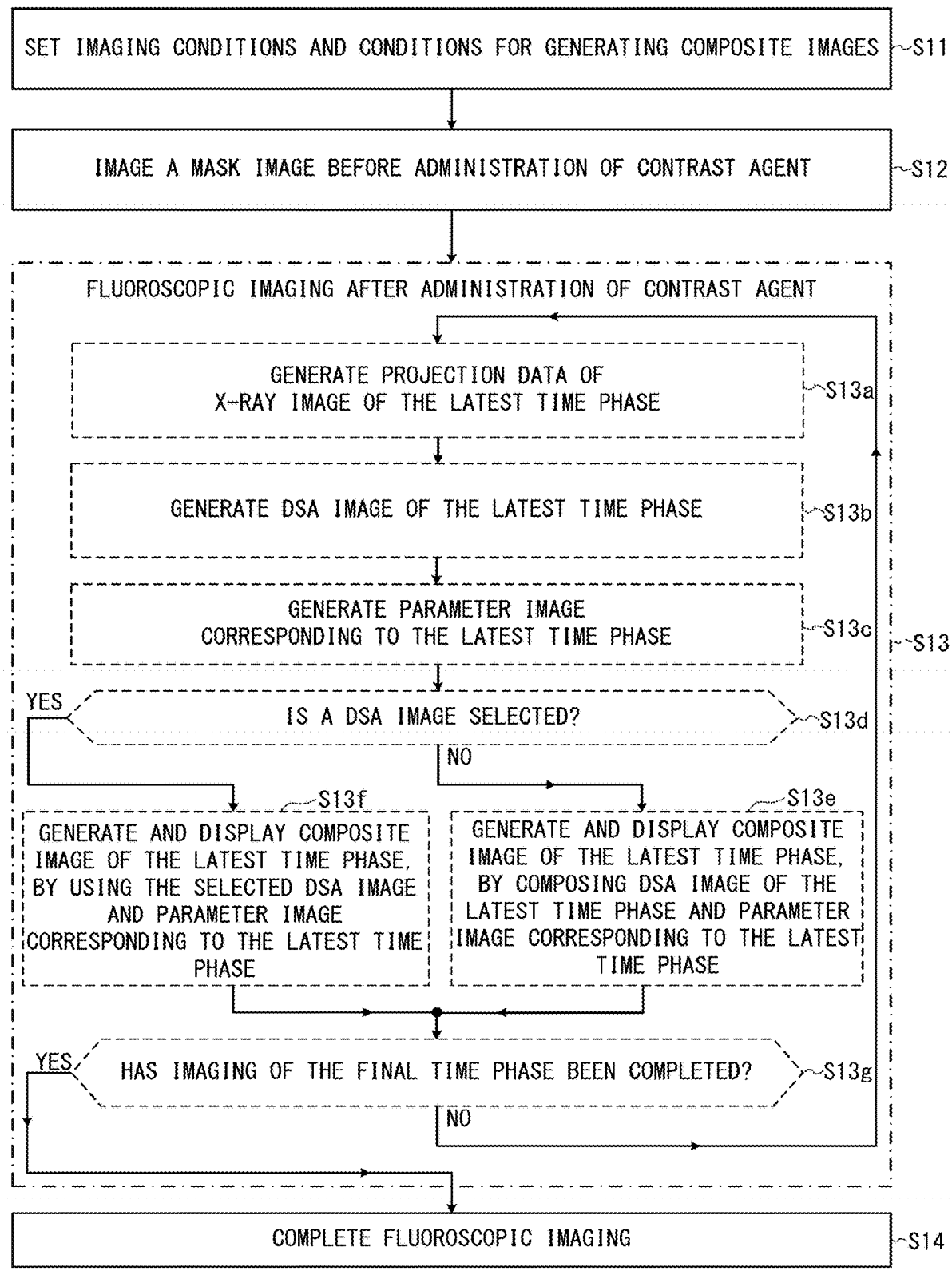
FIG. 8 is a flowchart showing an example of an operation of the X-ray diagnostic apparatus of the second embodiment, when composite images are updated and displayed to follow fluoroscopic imaging performed on a real-time basis.

FIG. 8 is a flowchart showing an example of an operation of the X-ray diagnostic apparatus 10 of the second embodiment, when composite images are updated and displayed to follow fluoroscopic imaging performed on a real-time basis. Hereinafter, according to the step numbers in the flowchart shown in FIG. 8, an operation of the X-ray diagnostic apparatus 10 will be explained.

[Step S11, S12] The processing in the Steps S11 and S12 is similar to the processing of the Steps S1 and S2 in the first embodiment. Afterward, the processing proceeds to the Step S13.

[Step S13] Fluoroscopic imaging and image display are performed on the same imaging region as the Step S12 according to the following detailed flow consisting of the Steps S13a to S13g. Incidentally, the display control unit 46d makes the display 47 update and display each of the DSA image of the latest time phase, the parameter image corresponding to the latest time phase, and a composite image.

The processing in the Steps S13a to S13c is similar to that of the Steps S3a to S3c in the first embodiment. Afterward, the processing proceeds to the Step S13d.

In the Step S13d, the composite image generation unit 46c determines whether one DSA image is selected via the input circuit 48 or not. When one DSA image is selected, the processing proceeds to the Step S13f. Otherwise, the processing proceeds to the Step S13e.

The processing in the Step S13e is similar to that of the Step S3d in the first embodiment.

In the Step S13f, the composite image generation unit 46c generates image data of a composite image of the latest time phase by composing image data of the DSA image of the time phase selected by a user and the parameter image corresponding to the latest time phase inputted from the parameter image generation unit 46b, according to the weight coefficients determined in the Step S11 (see FIG. 7). The composite image generation unit 46c outputs the image data of the composite image of the latest time phase to the display control unit 46d and stores the image data of the composite image of the latest time phase in the memory circuitry 44.

The display control unit 46d outputs the image data of the composite image of the latest time phase to the display 47, and controls the display 47 so that the currently displayed image is switched to the composite image of the latest time phase.

Afterward, the processing proceeds to the Step S13g.

In the Step S13g, whether imaging of the X-ray image of the final time phase has been completed or not is determined. If it has not been completed, the processing returns to the Step S13a. If it has been completed, the processing proceeds to the Step S14.

[Step S14] The processing of the Step S14 is the same as the Step S4 in the first embodiment.

The foregoing is the explanation of the flow shown in FIG. 8.

As a supplementary note, selection of a DSA image used for one of two original images for generating each composite image may be automatically performed by the composite image generation unit 46c at a predetermined timing, instead of manual processing by a user. The above-described predetermined timing may be set in the Step S21 to the timing when a half of the span from the administration of contrast agent to the end of fluoroscopic imaging just elapsed, as an example. Specifically, the composite image generation unit 46c preliminarily stores information on each imaging part (which part of a patient such as a chest, a head, etc. is imaged) and many examples of DSA images obtained by imaging the respective imaging parts in normal state. Then, the composite image generation unit 46c can select a DSA image which is greatly different from the preliminarily stored DSA image depicting the same imaging part in normal state, for example.

As mentioned above, the same effects as the first embodiment can be obtained in the second embodiment. Moreover, since one of two original images for generating each composite image is fixed to the DSA image of the time phase at which the candidate lesion region LS2 is most deeply projected in the second embodiment, it becomes easier to distinguish the position of the candidate lesion region LS2 in each composite image.

Then, composite images are sequentially generated by composing the selected DSA image and a parameter image, in which blood flow information included in a sequentially generated DSA image of the latest time phase is reflected, and these composite images are displayed in time-sequential order. Thus, a blood vessel flowing into the candidate lesion region LS2 and a blood vessel flowing out of the candidate lesion region LS2 can be distinguished by time-sequentially observing change in chromatic color of composite images to be sequentially updated. As a result, it becomes easier to distinguish a blood vessel flowing into a tumor and a blood vessel flowing out of a malformed part.

The Third Embodiment

Since the third embodiment is the same as the second embodiment except the difference described below, only the difference will be explained. In the third embodiment, one of two original images for generating each composite image of the latest time phase is unified to not a DSA image of a selected time phase but an average image of temporally consecutive DSA images of a selected span.

In the case of a post-process, a user can select a span, during which a candidate lesion region such as a tumor region is most deeply projected by contrast agent, via the input circuit 48.

Figure 9:
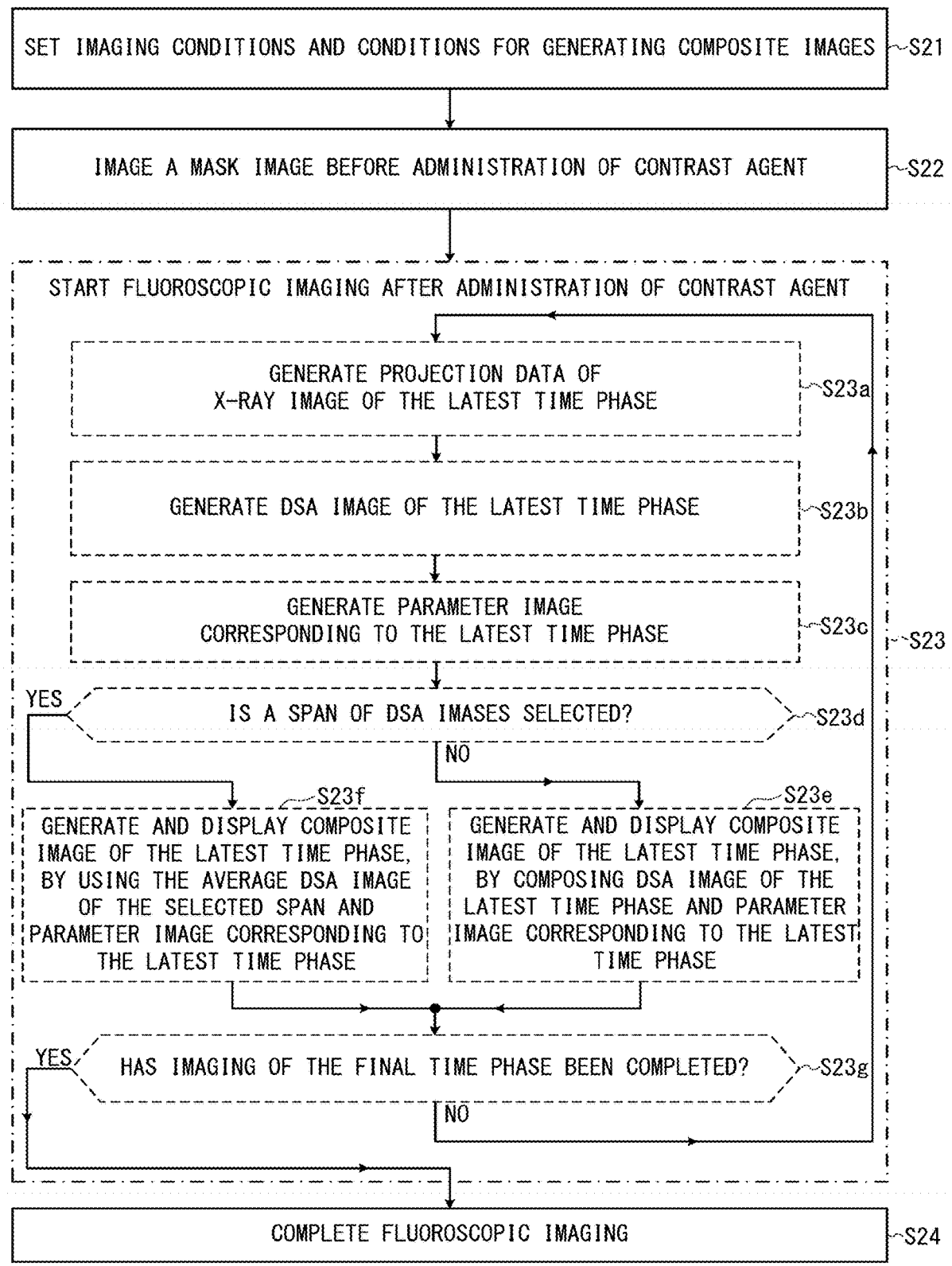
FIG. 9 is a flowchart showing an example of an operation of the X-ray diagnostic apparatus of the third embodiment, when composite images are updated and displayed to follow fluoroscopic imaging performed on a real-time basis.

FIG. 9 is a flowchart showing an example of an operation of the X-ray diagnostic apparatus 10 of the third embodiment, when composite images are updated and displayed to follow fluoroscopic imaging performed on a real-time basis. As an example here, until a span of DSA images is selected by a user's manipulation, the X-ray diagnostic apparatus 10 operates in a manner similar to the first embodiment. After selection of a span of DSA images, the X-ray diagnostic apparatus 10 switches to the operation mode of third embodiment.

[Step S21, S22] The processing in the Steps S21 and S22 is similar to the processing of the Steps S11 and S12 in the second embodiment. Afterward, the processing proceeds to the Step S23.

[Step S23] Fluoroscopic imaging and image display are performed on the same imaging region as the Step S22 according to the following detailed flow composed of the Steps S23a to S23g. The processing in each of the Steps S23a, S23b, S23c, S23e, and S23g is similar to the processing in each of the Steps S13a, S13b, S13c, S13e, and S13g in the second embodiment, respectively.

In the Step S23d, the composite image generation unit 46c determines whether a span of DSA images is selected or not. If it is selected, the processing proceeds to the Step S23f. Otherwise, the processing proceeds to the Step S23e.

In the Step S23f, the composite image generation unit 46c generates image data of a composite image of the latest time phase by composing (a) the average image of the DSA images in the span selected by a user and (b) the parameter image corresponding to the latest time phase inputted from the parameter image generation unit 46b, according to the weight coefficients determined in the Step S21. The composite image generation unit 46c outputs the image data of the composite image of the latest time phase to the display control unit 46d, and stores the image data of the composite image of the latest time phase in the memory circuitry 44.

[Step S24] The processing of the Step S24 is similar to that of the Step S14 in the second embodiment.

The foregoing is the explanation of the flow in FIG. 9.

In a manner similar to the above description, selection of a span of DSA images may be automatically performed by the composite image generation unit 46c instead of manual processing by a user.

As mentioned above, the same effects as the second embodiment can be obtained in the third embodiment.

The Fourth Embodiment

In the fourth embodiment, one of two original images for generating each composite image of the latest time phase is a DSA image of the latest time phase like the first embodiment, whereas the other of the two original images is unified to the parameter image obtained from the DSA images of all the time phases.

In the case of a post-process, one parameter image obtained from the DSA images of all the time phases (i.e. the parameter image corresponding to the final time phase) may be generated after completion of imaging of all the frames so that parameter image is used as one of the two original images for generating each composite image.

When composite images are updated and displayed on a real-time basis, the above-mentioned processing cannot be performed in the same manner but a parameter image as one of the two original images may be unified from certain time phases in the following manner. For example, a time phase, at which contrast agent concentration of each of a predetermined ratio of pixels out of all the pixels such as 50%, 60%, 70%, etc. exceeds the threshold value TH, may be determined as a provisionally final time phase for determining TTA of the predetermined ratio of pixels. Then, a unified parameter image may be generated from the DSA images from the first time phase to the provisionally final time phase, and this parameter image may be used as one of the two original images for generating each composite image after the provisionally final time phase.

Figure 10:
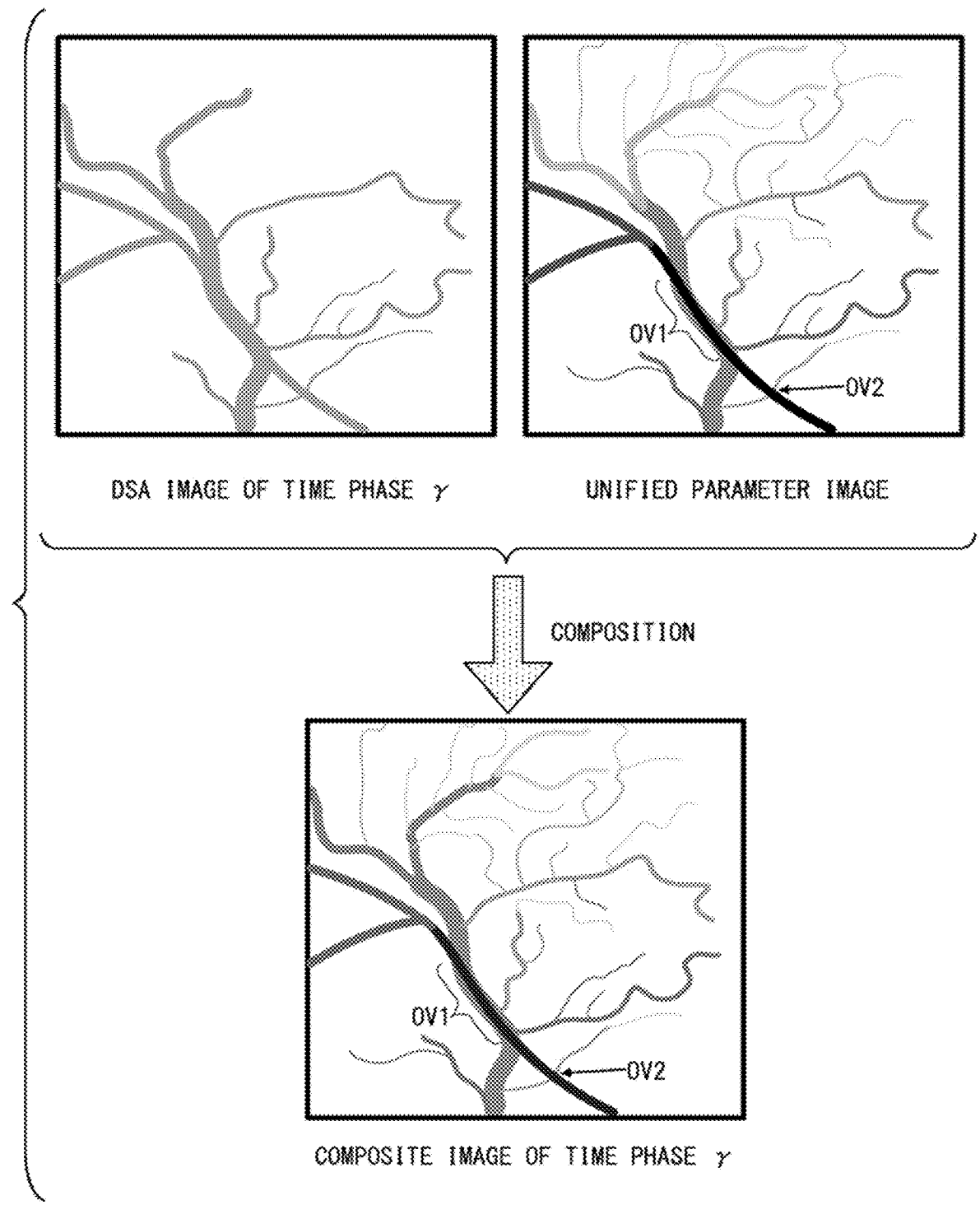
FIG. 10 is a schematic diagram showing an example of a composite image of a certain time phase γ generated based on a weighted average of the DSA image of the time phase γ and the unified parameter image obtained from DSA images of all the time phases, in the fourth embodiment.

FIG. 10 is a schematic diagram showing an example of a composite image of a certain time phase γ generated by calculating a weighted average of the DSA image of the time phase γ and the unified parameter image obtained from the DSA images of all the time phases, in the fourth embodiment. The left side of the upper part of FIG. 10 shows an example of the DSA image of the time phase γ, the right side of the upper part of FIG. 10 shows an example of the unified parameter image. The lower part of FIG. 10 shows an example of the composite image of these two images.

Each of overlay regions OV1 and OV2 in the upper part and lower part of FIG. 10 is a region, at which three-dimensionally separate two blood vessels are projected on a planar image so as to overlay each other.

In the DSA image of the time phase γ, contrast agent has not flow into capillary vessels and only thick blood vessels are projected as shown in the left side of the upper part of FIG. 10.

The parameter image on the right side of the upper part of FIG. 10 is drawn as a gray-scale schematic diagram for convenience like FIG. 4, so that a pixel with a lower TTA value is more blackly shown.

In the composite image shown in the lower part of FIG. 10, blood vessel regions, where contrast agent flows at the timing of the time phase γ, can be distinguished by averaging processing with the gray-scale DSA image. Moreover, it can be distinguished by difference in color reflected from the parameter image that two blood vessels exist in respective two positions mutually separated in the depth direction of the image in each of the overlay regions OV1 and OV2.

As to each pixel whose contrast agent concentration does not exceed the threshold value, its chromatic color cannot be determined based on the color map before the final time phase, when TTA is used as a parameter and each parameter image as one of the two original images for generating each composite image is sequentially updated.

However, information on blood flow change of all the time phases can be reflected by fixing one of two original images for generating each composite image to the parameter image corresponding to the final time phase. This is because the parameter image corresponding to the final time phase is generated based on temporal change of contrast agent concentration for each pixel obtained from the DSA images of all the time phases.

Thus, the fourth embodiment is suitable for a post-process, because information amount from the parameter image as one of two original images is always maximized and this makes observation of blood flow change easier in time-sequential display of the composite images from the first to the final time phases.

Since the other one of two original images for generating a composite image of each time phase is a DSA image of each time phase like the first embodiment, blood flow visible in a DSA image of the currently displayed time phase and temporal change information of blood flow in its surrounding region can be concurrently observed. By displaying such composite images in time-sequential order, a branch point of a blood vessel, overlay of blood vessels, etc. can be more easily recognized.

The Fifth Embodiment

Since the fifth embodiment is the same as the fourth embodiment except the flowing difference, only the difference will be explained. In the fifth embodiment, one of two original images for generating a composite image of the latest time phase is unified to not the parameter image corresponding to the final time phase but an average image of parameter images in a selected span.

Figure 11:
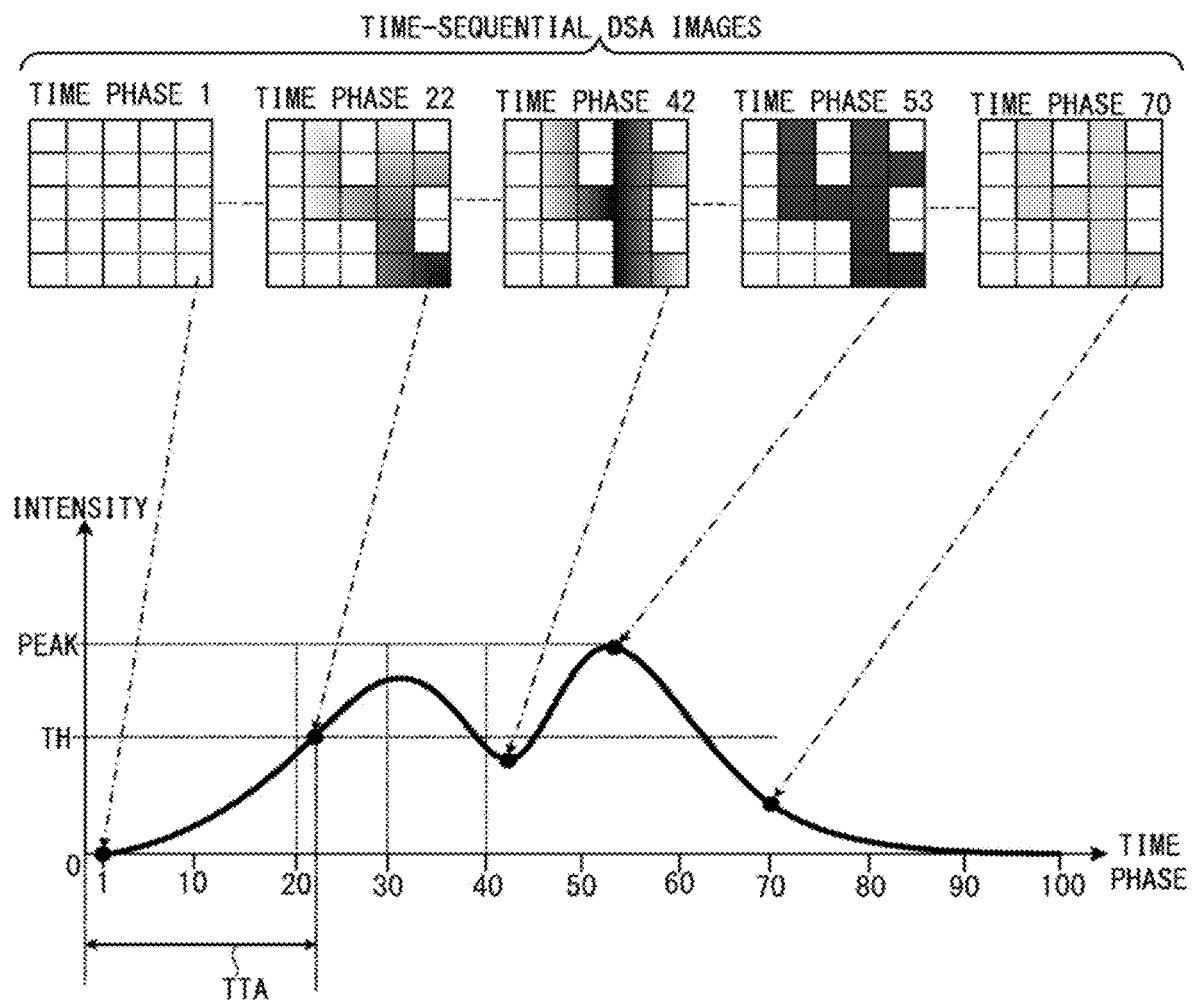
FIG. 11 is a schematic diagram showing an example of a method of determining parameter values based on span selection and temporal change of contrast agent concentration, in the fifth embodiment.

FIG. 11 a schematic diagram showing an example of a method of determining parameter values based on span selection and temporal change of contrast agent concentration, in the fifth embodiment. It is assumed that one hundred frames are imaged after administration of contrast agent and one hundred DSA images of one hundred time phases are generated as an example here. The upper part of FIG. 11 shows some of the one hundred time-sequential DSA images. As an example here, schematic diagrams of five DSA images corresponding to the respective time phases 1, 22, 42, 53, and 70 are shown in the upper part of FIG. 11.

The lower part of FIG. 11 shows an example of temporal change of contrast agent concentration of one target pixel positioned at the bottom-right corner in each of the DSA images of all the time phases in a manner similar to that of the middle part of FIG. 2. As mentioned above, if appropriate processing such as sign inversion etc. is performed on change of pixel values of a target pixel over time phases, this change of pixel values becomes equal to temporal change of contrast agent concentration of this pixel.

When a span from the time phases 20 to 30 is selected via the input circuit 48 as an example, the parameter value acquisition unit 46a determines parameter values (of TTA in this example) in the span from the time phases 20 to 30. More specifically, since contrast agent concentration exceeds the threshold value TH at the time phase 22 in the span from the time phases 20 to 30, the parameter value of TTA of the pixel positioned at the bottom-right corner becomes 22.

When a span from the time phases 30 to 40 is selected via the input circuit 48 as an example, contrast agent concentration exceeds the threshold value TH at the first time phase 30. In this case, the parameter value acquisition unit 46a determines the parameter value of TTA of the pixel positioned at the bottom-right corner as 30. Similar processing is performed on all of the rest of the pixels in the span from the time phases 30 to 40, and thereby parameter values of all the pixels are determined.

The parameter image generation unit 46b generates image data of one unified parameter image based on the color map and the parameter value of the selected span determined for each pixel in the above manner.

In the case of a post-process, the display control unit 46d makes the display 47 display respective parameter images corresponding to all the time phases in time-sequential order, for example. In this case, a user can select a span of parameter images used for one of original images for generating a composite image by designating time phases via the input circuit 48.

Figure 12:
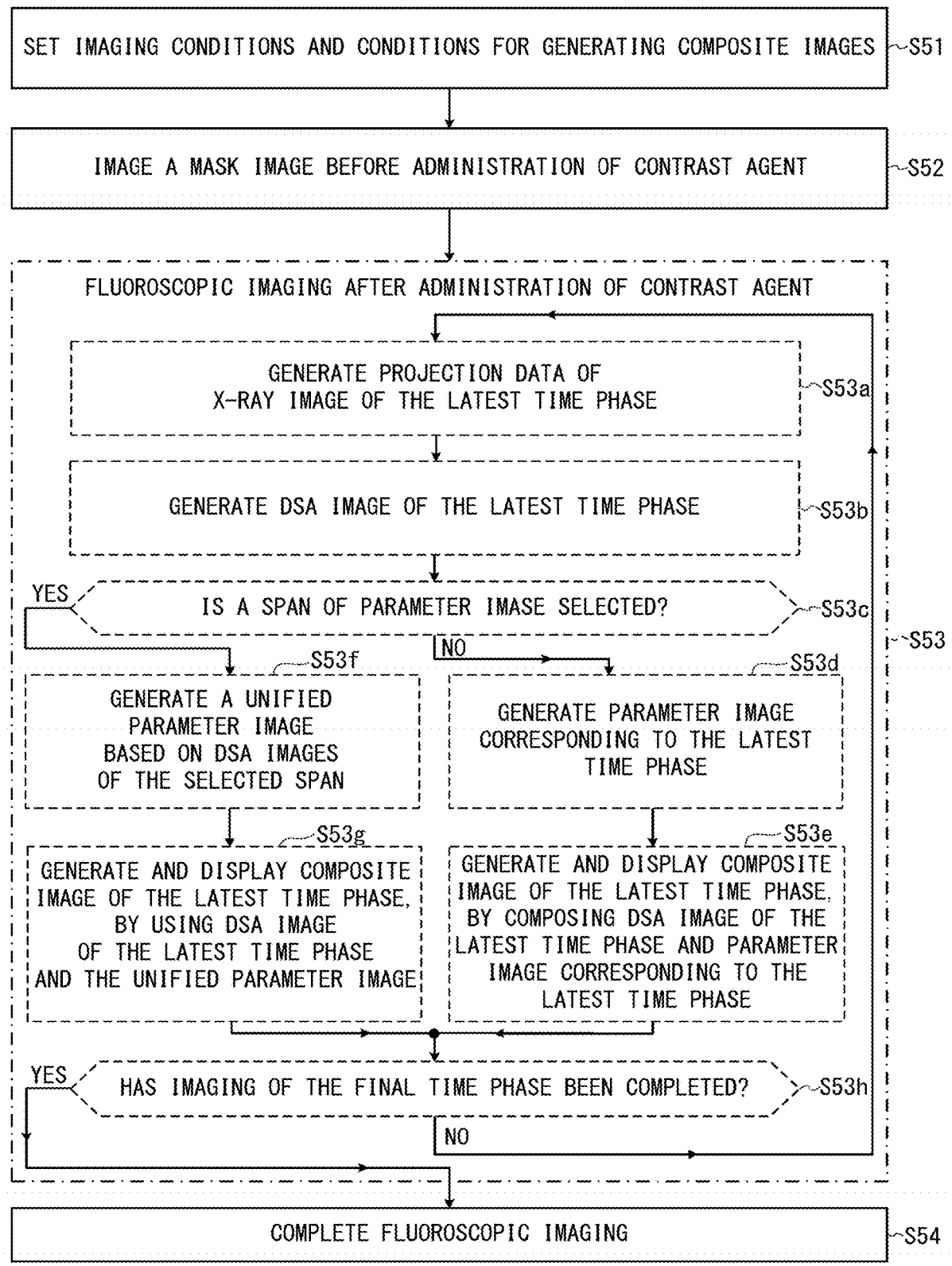
FIG. 12 is a flowchart showing an example of an operation of the X-ray diagnostic apparatus of the fifth embodiment, when composite images are updated and displayed to follow fluoroscopic imaging performed on a real-time basis.

FIG. 12 is a flowchart showing an example of an operation of the X-ray diagnostic apparatus 10 of the fifth embodiment, when composite images are updated and displayed to follow fluoroscopic imaging performed on a real-time basis. As an example here, the X-ray diagnostic apparatus 10 operates in a manner similar to the first embodiment until a span of DSA images is selected by a user's input, and switches to the operation mode of the fifth embodiment after selection of the span.

[Step S51, S52] The processing in the Steps S51 and S52 is similar to the processing in the Steps S11 and S12 in the second embodiment. Afterward, the processing proceeds to the Step S53.

[Step S53] Fluoroscopic imaging and image display are performed on the same imaging region as the Step S52 according to the following detailed flow composed of the Steps S53a to S53h.

The processing in each of the Steps S53a, S53b, S53e, and S53h is similar to the processing in each of the Steps S13a, S13b, S13e, and S13g in the second embodiment, respectively.

In the Step S53c, the parameter value acquisition unit 46a determines whether a span of parameter images is selected via the input circuit 48 or not. If the span is selected, the processing proceeds to the Step S53f. Otherwise, the processing proceeds to the Step S53d.

In the Step S53d, the parameter value acquisition unit 46a and the parameter image generation unit 46b generate the image data of a parameter image corresponding to the latest time phase in a manner similar to that of the first embodiment, store the generated image data in the memory circuitry 44, and output the generated image data to the composite image generation unit 46c.

Afterward, the processing proceeds to the Step S53e.

The processing content of the Step S53f is divided into the following two cases, depending on whether a span is selected for the first time or again.

Firstly, when a span is selected for the first time, the parameter value acquisition unit 46a determines a parameter value for each pixel based on the image data of the DSA images of the selected span as mentioned above, and outputs the determined parameter values to the parameter image generation unit 46b. The parameter image generation unit 46b generates the image data of one unified parameter image based on the color map and the inputted parameter values of the respective pixels in the selected span. The parameter image generation unit 46b stores the image data of the unified parameter image in the memory circuitry 44, and outputs the image data of the unified parameter image to the composite image generation unit 46c. Afterward, the processing proceed to the Step S53g.

Secondly, when the processing returns to this Step S53f again after a span is selected for the first time and then imaging of the next time phase is performed by way of the Steps S53g and S53h, the processing proceeds to the Step S53g without performing substantial processing. This is because the image data of one unified parameter image have been already generated in this case.

In the Step S53g, the composite image generation unit 46c generates the image data of the composite image of the latest time phase by composing the image data of the unified parameter image and the image data of the DSA image of the latest time phase, according to the weight coefficients determined in the Step S51. The composite image generation unit 46c output the image data of the composite image of the latest time phase to the display control unit 46d, and stores the image data of the composite image of the latest time phase in the memory circuitry 44.

[Step S54] The processing of the Step S54 is the same as the processing of the Step S14 in the second embodiment.

The foregoing is the explanation of the flow of FIG. 12.

The fifth embodiment is effective for a case where observation of parameter images of only limited time phases excluding several frames in the beginning and several frames in the ending is desired. As mentioned above, the same effects as the fourth embodiment can be also obtained in the fifth embodiment.

The Sixth Embodiment

In the first to fifth embodiments, examples in which each composite image of a DSA image and a parameter image is generated has been explained. In the sixth embodiment, a non-contrast image on which an instrument is projected is used for generation of each composite image instead of DSA images. The above-described instrument means a surgical instrument inserted into inside of a blood vessel such as a guidewire etc.

In the sixth embodiment, first, DSA images and parameter images are generated and stored by the first fluoroscopic imaging with administration of contrast agent. In this first fluoroscopic imaging, the X-ray diagnosis apparatus 10 operates so as to realize fluoroscopic imaging on the same imaging region of the same object P again, by fixing or storing positions of the C-arm 33, the table 22, etc.

Next, in the second fluoroscopic imaging as non-contrast imaging on the same imaging region of the same object P, a composite image of the latest X-ray image sequentially generated on a real-time basis and a parameter image stored after completion of the first imaging is updated and displayed. In the second fluoroscopic imaging, each composite image is used as a roadmap so that a guidewire as an example is operated inside the object P.

Figure 13:
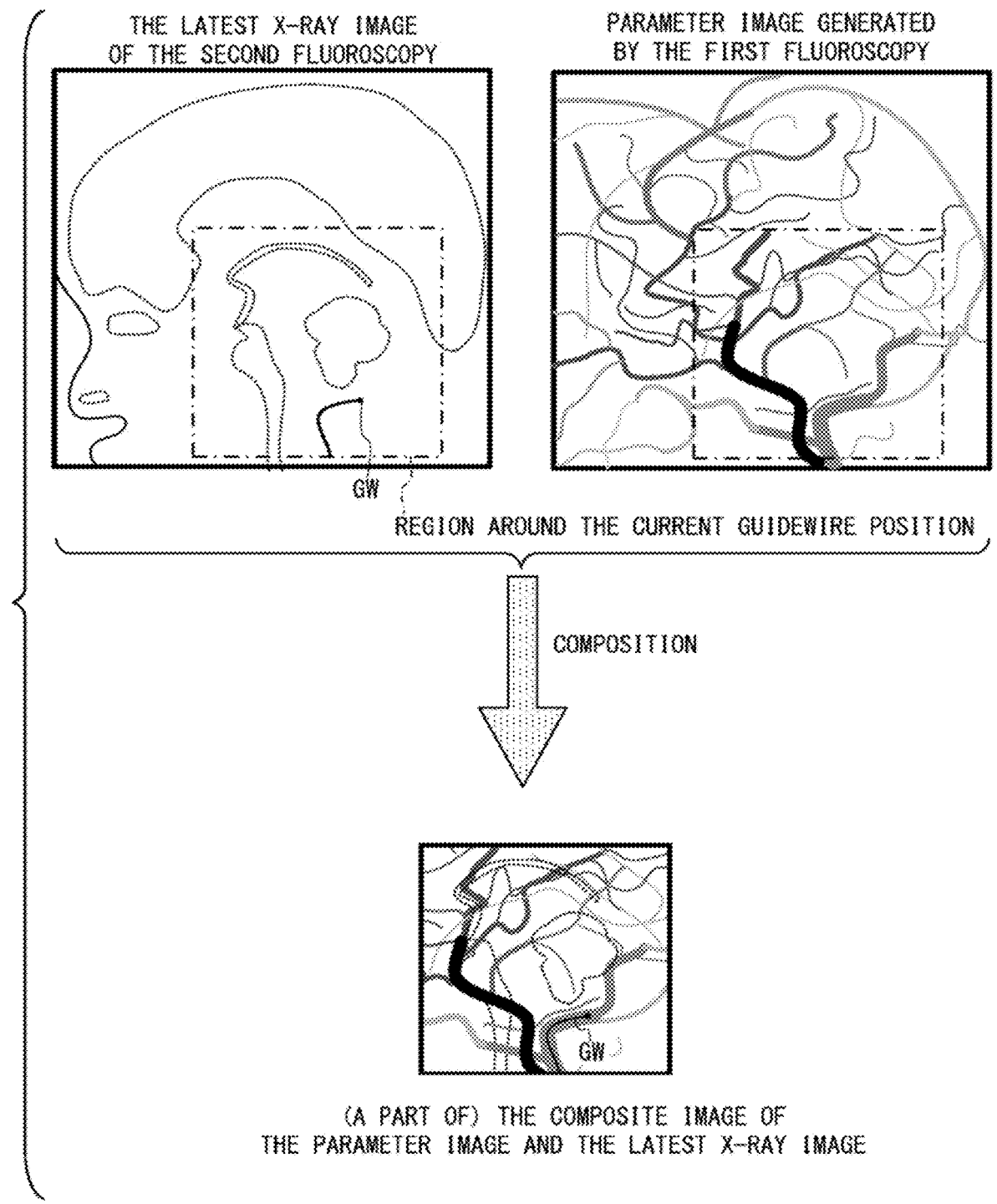
FIG. 13 is a schematic diagram showing an example of a composite image generated by composing a parameter image stored in the first fluoroscopic imaging and the latest X-ray image of the second fluoroscopic imaging, in the sixth embodiment.

FIG. 13 a schematic diagram showing an example of a composite image generated by composing a parameter image stored in the first fluoroscopic imaging and the latest X-ray image of the second fluoroscopic imaging, in the sixth embodiment. The left side of the upper part of FIG. 13 shows an example of the latest X-ray image in the second fluoroscopic imaging as non-contrast imaging, and blood vessels are not projected in this X-ray image due to non-contrast imaging. Each frame shown by chain lines in the left and right sides of the upper part of FIG. 13 is a peripheral region of the guidewire GW to be operated (region of interest).

The right side of the upper part of FIG. 13 shows an example of a parameter image generated from temporal change of contrast agent concentration for each pixel obtained from the DSA images of all the time phases of the first fluoroscopic imaging with the use of contrast agent. The right side of the upper part of FIG. 13 is drawn as a gray-scale schematic diagram for convenience like FIG. 4 so that a pixel with a lower TTA value is more blackly displayed.

The lower part of FIG. 13 shows an example of the composite image of these two images. As an example here, the lower part of FIG. 13 shows only the region surrounded by chain lines in the latest X-ray image shown on the left side of the upper part of FIG. 13. As methods of composition, for example, the following methods can be used.

Firstly, the region of the instrument (guidewire GW in this example) to be operated is extracted from each latest X-ray image time-sequentially generated on a real-time basis in the second fluoroscopic imaging, by a known image processing technique such as pattern matching etc. After alignment of the latest X-ray image and the parameter image, only the extracted pixel region indicating the instrument is inserted into the parameter image so that the extracted pixel region is inserted into the same position as the original latest X-ray image and each pixel of the inserted pixel region keeps the same gray-scale pixel value. Since positions of the C-arm 33, the table 22, etc. are commonly fixed between the first fluoroscopic imaging for generating a parameter image and the second fluoroscopic imaging as non-contrast imaging as mentioned above, positional displacement hardly occurs.

Secondly, a simple average of a DSA image and a parameter image may be determined as a composite image.

Thirdly, a weighted average of a DSA image and a parameter image may be determined as a composite image. It is assumed that weights of a DSA image and a parameter image can be arbitrarily set via the input circuit 48.

The lower part of FIG. 13 shows an example of a composite image generated by weighted average processing. Although the parameter image on the right side in the upper part of FIG. 13 and the composite image in the lower part of FIG. 13 are shown as gray-scale images for convenience, actually these are displayed as color images including various chromatic colors. Since the guidewire GW is (blackly) displayed under gray-scale inside blood vessels displayed with chromatic colors in each composite image, the position of the guidewire GW can be easily recognized in each composite image.

In addition, temporal change of blood flow appears as change in color in each composite image. Thus, a region whose color is close to the color of the current tip position of the guidewire GW can be judged as a blood vessel region directly linked to the current tip position, i.e. a region to which the guidewire GW can be advanced.

As to a blood vessel which seems to intersect or branch on a two-dimensional composite image, it can be judged as two of three-dimensionally separate blood vessels if color of one part of this blood vessel is greatly different from another part of this blood vessel on the two-dimensional composite image. Additionally, as to a blood vessel which seems to intersect or branch on a two-dimensional composite image, it can be judged as a branch point of one blood vessel if color of this blood vessel on the two-dimensional composite image is substantially uniform. Such a judgment result as described above clarifies the direction to which the guidewire GW should be advanced.

Figure 14:
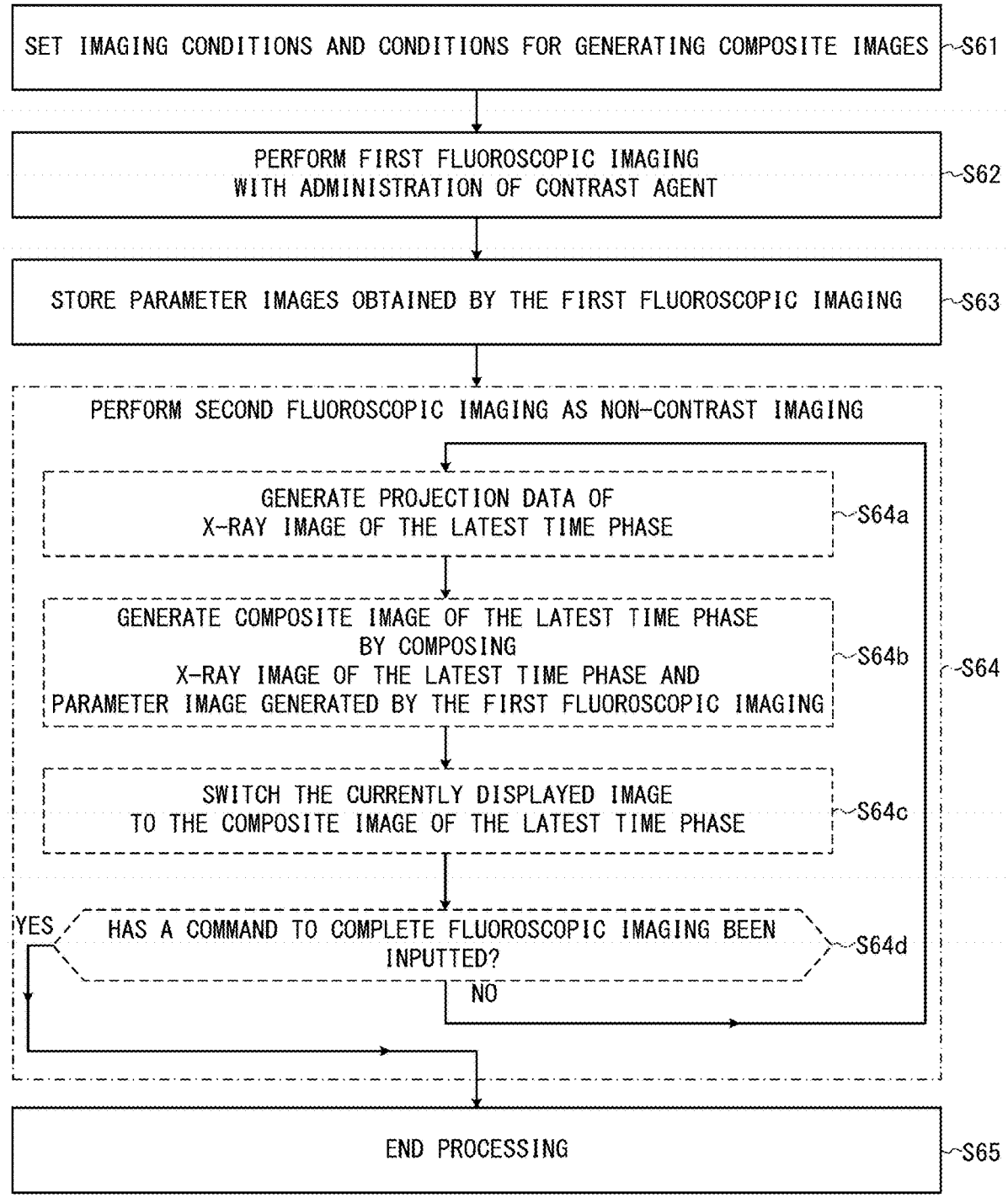
FIG. 14 is a flowchart showing an example of an operation of the X-ray diagnostic apparatus of the sixth embodiment, when composite images are updated and displayed to follow fluoroscopic imaging performed on a real-time basis.

FIG. 14 is a flowchart showing an example of an operation of the X-ray diagnostic apparatus 10 of the sixth embodiment, when composite images are updated and displayed to follow fluoroscopic imaging performed on a real-time basis. Hereinafter, according to the step numbers in the flowchart shown in FIG. 14, an operation of the X-ray diagnostic apparatus 10 will be explained.

[Step S61] Some of imaging conditions of the first fluoroscopic imaging with administration of contrast agent, some of imaging conditions of the second fluoroscopic imaging as non contrast imaging, and conditions for generating composite images are inputted by a user via the input circuit 48.

The system control unit 42a (FIG. 1) determines all the imaging conditions of the first fluoroscopic imaging according to the inputted imaging conditions. In addition, the parameter value acquisition unit 46a determines the parameter (TTA in this example) according to the inputted conditions, and the parameter image generation unit 46b determines the unified color map over all the time phases according to the determined parameter and imaging conditions such as frame number etc.

Afterward, the processing proceeds to the Step S62.

[Step S62] The imaging region of the object P is fixed from the start of the first fluoroscopic imaging to the end of the second fluoroscopic imaging. In the Step S62, projection data of an X-ray image before administration of contrast agent (i.e. image data of a mask image) are generated in a similar manner as described above, and the generated projection data are stored in the memory circuitry 44. After this, contrast agent is administered to the object P by remote operation of a non-illustrated contrast agent administration device, and then projection data of X-ray images of a large number of time-sequential time phases are generated and stored in the memory circuitry 44 in a similar manner as described above.

Afterward, the processing proceeds to the Step S63.

[Step S63] The DSA image generation unit 42c generates image data of respective DSA images corresponding to all the time phases after the administration of contrast agent and stores the generated image data in the memory circuitry 44 in a similar manner as described above. In addition, the parameter value acquisition unit 46a calculates change of contrast agent concentration from the first time phase to the final time phase for each pixel of each DSA image and outputs this calculation result to the parameter image generation unit 46b. The parameter image generation unit 46b generates one unified parameter image based on the change of contrast agent concentration from the first time phase to the final time phase, and stores the image data of this parameter image in the memory circuitry 44.

Afterward, the processing proceeds to the Step S64.

[Step S64] While positions of the table 22, the C-arm 33, etc. are fixed, the guidewire GW inserted into inside of a blood vessel of the same object P is advanced to a position close to the imaging region of the Step S62 and then the second fluoroscopic imaging as non-contrast imaging is performed according to the following detailed flow composed of the Steps S64a to S64d.

In the Step S64a, each component of the X-ray diagnostic apparatus 10 operates so as to generate projection data of X-ray images and stores them in the memory circuitry 44, in a similar manner as described above.

Afterward, the processing proceeds to the Step S64b.

In the Step S64b, the composite image generation unit 46c generates image data of a composite image of the latest time phase by composing the latest X-ray image generated and stored in the Step S64a and the parameter image stored in the Step S63, according to the conditions for generating each composite image determined in the Step S61 (see FIG. 13). The composite image generation unit 46c outputs the image data of the composite image of the latest time phase to the display control unit 46d, and stores the image data of the composite image of the latest time phase in the memory circuitry 44.

Afterward, the processing proceeds to the Step S64c.

In the Step S64c, the display control unit 46d outputs the image data of the composite image of the latest time phase to the display 47 and makes the display 47 switch its display image to the composite image of the latest time phase.

Afterward, the processing proceeds to the Step S64d.

In the Step S64d, the system control unit 42a determines whether a command to complete the second fluoroscopic imaging is inputted via the input circuit 48 or not. If it is inputted, the processing returns to the Step S64a. Otherwise, the processing proceeds to the Step S65.

In other words, processing of (a) sequentially generating X-ray images on a real-time basis, (b) updating the composite image between the unified parameter image and the latest X-ray image, and (c) displaying the updated composite image as a roadmap is repeated until the command to complete the second fluoroscopic imaging is inputted.

In addition, an operator advances the guidewire GW to a target position by manipulating the guidewire operating device 200 with reference to the updated and displayed composite image as a roadmap, while the second fluoroscopic imaging is performed.

Although the processing of the Step S64 is divided into the Steps S64a to S64d in order to simplify the explanation here, this is only an example and should not be interpreted as limiting the present disclosure. In other words, the imaging operation in the Step S64a is independently performed according to determined imaging interval, regardless of progress status of the processing of updating and displaying each composite image in the Steps S64b and S64c.

[Step S65] The system control unit 42a controls each component of the X-ray diagnostic apparatus 10 so that operation of the second fluoroscopic imaging is completed.

The foregoing is the explanation of the operation of the sixth embodiment. The difference between conventional technology and the sixth embodiment is explained as follows.

In conventional technology, a subtraction image in which blood vessels are selectively whitely depicted is generated based on difference between an X-ray image generated in the first fluoroscopic imaging in which blood vessels are selectively imaged by contrast agent and the latest non-contrast X-ray image generated in the second fluoroscopic imaging (in which a guidewire is projected, for example). Since a roadmap in the conventional technology is generated by overlaying such a subtraction image on the latest X-ray image, it is a gray-scale image.

By contrast, in the sixth embodiment, each composite image is obtained by composing the latest non-contrast X-ray image of the second fluoroscopic imaging and the parameter image on which blood flow information included in all the time phases of the first fluoroscopic imaging is reflected, and such a composite image is updated and displayed as a roadmap. Since a blackly projected guidewire GW is depicted inside a blood vessel region displayed with chromatic colors in the sixth embodiment, the guidewire GW in each composite image is clearly distinguished by difference in color.

In addition, temporal change of blood flow appears as change in color in each composite image in the sixth embodiment. Thus, a region whose color is close to the color of the current tip position of the guidewire GW can be easily judged as a blood vessel region directly linked to the current tip position, i.e. a region to which the guidewire GW can be advanced.

As to a blood vessel which seems to intersect or branch on a two-dimensional composite image, it can be judged as two of three-dimensionally separate blood vessels if color of one part of this blood vessel is greatly different from another part of this blood vessel on the two-dimensional composite image. Additionally, as to a blood vessel which seems to intersect or branch on a two-dimensional composite image, it can be judged as a branch point of one blood vessel if color of this blood vessel on the two-dimensional composite image is substantially uniform. Accordingly, the direction to which the guidewire GW should be advanced is clarified and thus it is expected that an operator can manipulate the guidewire GW more deftly than conventional technology. As a result, it is expected that the second fluoroscopic operation is completed in a shorter time which leads to reduction of dose and reduction of burden on a patient According to each of the above-described embodiments, a region of a blood vessel and a branch point of a blood vessel can be observed more satisfactorily than the conventional technology (regardless of contrast agent amount, even in a case where blood vessels can be visualized only in a temporally limited span in DSA images due to transient inflow of contrast agent as an example).

Supplementary Notes on Embodiments

[1] In each of the above-described embodiments, an example in which the DSA image generation unit 42c generates image data of DSA images and (the parameter value acquisition unit 46a etc. of) the image processing device 46 acquires projection data of respective X-ray images before and after administration of contrast agent from the memory circuitry 44 has been explained. However, embodiments of the present disclosure are not limited to such an aspect. For example, the X-ray diagnostic apparatus 10 may be configured so that the DSA image generation unit 42c is disposed not inside the imaging control device 42 but inside the image processing device 46 and generates image data of DSA images in a similar manner.

[2] In each of the above-described embodiments, an example in which the image processing device 46 is installed in the X-ray diagnostic apparatus 10 has been explained. However, embodiments of the present disclosure are not limited to such an aspect. The image processing device 46 may be installed in another image diagnosis apparatus capable of imaging blood flow images before and after administration of contrast agent such as an X-ray CT (Computed Tomography) apparatus and a magnetic resonance imaging apparatus, for example.

[3] In each of the above-described embodiments, an example in which respective composite images etc. are displayed on the display 47 connected to the image processing device 46 by the display control function of the display control unit 46d has been explained. However, embodiments of the present disclosure are not limited to such an aspect. The display 47 may be configured as one component of the image processing device 46.

[4] An image processing program may be generated by coding the processing from the Step S3a to S3e in FIG. 6 of the first embodiment. The image processing device 46 in FIG. 1 may be interpreted as a device in which such an image processing program is installed. As to each of the second to the sixth embodiments, an image processing program may be generated in a similar manner as described above.

Although, the imaging control device 42 and the image processing device 46 are explained as hardware in FIG. 1, each of the imaging control device 42 and the image processing device 46 may be configured as processing circuitry equipped with at least a processor and a memory circuit. In this case, the image processing device 46 implements the parameter value acquisition function (46a), the parameter image generation function (46b), a composite image generation function (46c), and the display control function (46d), by making its processor execute the above-described image processing program stored in the memory circuit. Each of these functions is stored in the form of program in the memory circuit. The same holds true for the imaging control device 42.

The above-described term "processor" means, for instance, a circuit such as a dedicated or general-purpose CPU (Central Processing Unit), a dedicated or general-purpose GPU (Graphics Processing Unit), an ASIC (Application Specific Integrated Circuit), a programmable logic device including an SPLD (Simple Programmable Logic Device) as an example, a CPLD (Complex Programmable Logic Device), an FPGA (Field Programmable Gate Array), and so on. A processor Implements various types of functions by reading out programs stored in memory circuitry and implementing the programs.

In addition, programs may be directly installed in the circuit of a processor instead of storing programs in the memory circuitry. In this case, the processor implements various types of functions by reading out programs stored in its own circuit and executing the programs.

Furthermore, single processing circuitry may implements each function. The processing circuitry may be configured by combining mutually independent processors each of which implements each function of the processing circuitry by executing a program.

When plural processors are provided, a memory medium for storing programs may be disposed for each processor, or a single memory circuit may collectively store the programs corresponding to the functions of all the processors.

[5] Correspondences between terms used in the claims and terms used in the embodiment described above will be described. Note that the correspondence described below is possible interpretation for reference and should not be construed as limiting the present invention.

The entirety of the bed device 20, the X-ray generating and detecting system 30, and the imaging control device 42 which generates projection data of X-ray images and image data of DSA images by performing X-ray imaging on an object is an example of the X-ray imaging device described in the claims.

[6] While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An image processing device, comprising:
    processing circuitry configured to
        sequentially acquire image data of a DSA image of time-sequential DSA images of an object,
        sequentially acquire, each time image data of a DSA image of a latest time phase is acquired, a parameter value for each pixel based on a temporal change of a pixel value of each pixel corresponding to a same region of the object in the sequentially acquired image data of the DSA image of the time-sequential DSA images of the object, the parameter value at each pixel being a value that represents a time at which a parameter satisfies a predetermined condition defined for the parameter and the parameter value at each pixel being a value that is fixed for each of the sequentially acquired image data as it is sequentially acquired and does not change thereafter, and
        sequentially generate, each time the image data of the DSA image of the latest time phase is acquired, image data of a parameter image in such a manner that identification information according to the parameter value of each pixel is assigned to each pixel corresponding to the same region.

2. The image processing device according to claim 1, wherein the processing circuitry is further configured to make a display sequentially display the parameter images based on the image data of parameter images.

3. The image processing device according to claim 1, wherein the processing circuitry is further configured to:
    sequentially acquire the image data of the DSA image of the time-sequential DSA images generated in real-time by fluoroscopic imaging on the object,
    sequentially generate, each time the image data of the DSA image of the latest time phase is acquired, image data of parameter images such that each of the parameter images reflects image data of the DSA image of a corresponding latest time phase, and
    sequentially generate, each time the image data of the DSA image of the latest time phase is acquired, image data of a composite image, wherein the composite image is obtained by composing the DSA image and the parameter image corresponding to the latest time phase.

4. The image processing device according to claim 3, wherein the processing circuitry is further configured to sequentially generate the composite image data of the composite image by composing the parameter image corresponding to the latest time phase and the DSA image of the latest time phase.

5. The image processing device according to claim 3, wherein the processing circuitry is further configured to sequentially generate composite image data of composite images, each of which is obtained by composing a representative DSA image commonly used for generating the composite images and the parameter image corresponding to the latest time phase.

6. The image processing device according to claim 3, wherein the processing circuitry is further configured to sequentially generate composite image data of composite images, each of which is obtained by composing an average image of DSA images of consecutive time phases commonly used for generating the composite images and the parameter image corresponding to the latest time phase.

7. The image processing device according to claim 3, wherein the processing circuitry is further configured to generate image data of a unified parameter image in which acquired image data of DSA images of all time phases are reflected, and
    generate composite image data of composite images corresponding to respective DSA images, by composing the unified parameter image and each of the DSA images.

8. The image processing device according to claim 3, wherein the processing circuitry is further configured to generate image data of a unified parameter image in such a manner that DSA images of consecutive time phases as a part of acquired DSA images of all time phases are reflected, and
    generate composite image data of composite images corresponding to respective DSA images, by composing the unified parameter image and each of the DSA images.

9. The image processing device according to claim 1, wherein the processing circuitry is further configured to
acquire a first time phase, at which a contrast agent concentration exceeds a threshold value, as the parameter value.

10. The image processing device according to claim 1, wherein the processing circuitry is further configured to
sequentially generate the image data of parameter images, by coloring each pixel corresponding to the same region of the object according to the parameter value.

11. An X-ray diagnostic apparatus, comprising:
an X-ray imaging device configured to generate projection data of time-sequential X-ray images by detecting X-rays passing through an object before and after administration of a contrast agent, and generate image data of time-sequential DSA images of the object based on each subtraction between an X-ray image before the administration of the contrast agent and each of time-sequential X-ray images after the administration of the contrast agent; and
the image processing device according to claim 1.

12. The image processing device of claim 1, wherein the processing circuitry is further configured to generate the image data of the parameter image so that, for each pixel in the parameter image, the identification information is determined and fixed based on a corresponding parameter value of the pixel.

13. The image processing device of claim 1, wherein
the parameter value for each pixel of a third DSA image of the time-sequential DSA images is generated based upon the temporal change over a first time phase through a third time phase corresponding to a first DSA image through the third DSA image of the time-sequential DSA images, respectively, and does not change thereafter, and
the parameter value for each pixel of a fourth DSA image of the time-sequential DSA images is generated based upon the temporal change over the first time phase through a fourth time phase corresponding to the first DSA image through a fourth DSA image of the time-sequential DSA images, respectively, and does not change thereafter.

14. The image processing device of claim 13, wherein
a third parameter image is generated based upon the parameter value for each pixel of the third DSA image and a unified color table, and
a fourth parameter image is generated based upon the parameter value for each pixel of the fourth DSA image and the unified color table.

15. An image processing method, comprising:
sequentially acquiring image data of a DSA image of time-sequential DSA images of an object,
sequentially acquiring, each time image data of a DSA image of a latest time phase is acquired, a parameter value for each pixel based on a temporal change of a pixel value of each pixel corresponding to a same region of the object in the sequentially acquired image data of the DSA image of the time-sequential DSA images of the object, the parameter value being a value that represents a time at which a parameter satisfies a predetermined condition defined for the parameter and the parameter value at each pixel being a value that is fixed for each of the sequentially acquired image data as it is sequentially acquired and does not change thereafter, and
sequentially generating, each time the image data of the DSA image of the latest time phase is acquired, image data of a parameter image in such a manner that identification information according to the parameter value is assigned to each pixel corresponding to the same region.

* * * * *